United States Patent
Berenfeld

(10) Patent No.: US 11,844,615 B2
(45) Date of Patent: Dec. 19, 2023

(54) CATHETER AND METHOD TO LOCALIZE ECTOPIC AND REENTRANT ACTIVITY IN THE HEART

(71) Applicant: THE REGENTS OF THE UNIVERSITY OF MICHIGAN, Ann Arbor, MI (US)

(72) Inventor: Omer Berenfeld, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1496 days.

(21) Appl. No.: 15/042,681

(22) Filed: Feb. 12, 2016

(65) Prior Publication Data
US 2016/0262647 A1 Sep. 15, 2016

Related U.S. Application Data

(60) Provisional application No. 62/132,218, filed on Mar. 12, 2015.

(51) Int. Cl.
*A61B 5/287* (2021.01)
*A61B 5/00* (2006.01)
(Continued)

(52) U.S. Cl.
CPC .............. *A61B 5/287* (2021.01); *A61B 5/339* (2021.01); *A61B 5/361* (2021.01); *A61B 5/364* (2021.01);
(Continued)

(58) Field of Classification Search
CPC ..... A61B 5/0422; A61B 5/044; A61B 5/0468; A61B 5/6852; A61B 5/04017;
(Continued)

(56) References Cited

U.S. PATENT DOCUMENTS 6,839,588 B1 * 1/2005 Rudy ................... A61B 5/0422
600/508
6,892,091 B1 * 5/2005 Ben-Haim ........... A61B 5/0422
600/509

(Continued)

FOREIGN PATENT DOCUMENTS

| WO | WO-2005/115232 A1 | 12/2005 |
|---|---|---|
| WO | WO-2008/039968 A2 | 4/2008 |
| WO | WO-2011/127209 A1 | 10/2011 |

OTHER PUBLICATIONS

Atienza et al., Translational research in atrial fibrillation: a quest for mechanistically based diagnosis and therapy, Circ. Arrhythm Electrophysiol., 5(6):1207-15 (2012).

(Continued)

*Primary Examiner* — Eun Hwa Kim
*Assistant Examiner* — Catherine Premraj
(74) *Attorney, Agent, or Firm* — MARSHALL, GERSTEIN & BORUN LLP

(57) ABSTRACT

Techniques are provided that identify and localize on to reentrant and ectopic patterns of electrical activation in the heart wall. These patterns may correspond to atrial fibrillation, ventricular fibrillation, or other heart arrhythmia conditions. The techniques detect these patterns of electrical activity using a multi-lead an intra-cavitary catheter that, along with a controller, is able to track, over a multi-dimensional cubic space, reentrant activity and identify filaments in the heart cavity. The intra-cavitary catheter includes multiple conducting poles positioned in a configuration relative to each other and functioning as either or both sensing and active poles for measuring electrical pathways in the heart wall and over the multi-dimensional space.

23 Claims, 23 Drawing Sheets
(10 of 23 Drawing Sheet(s) Filed in Color)

(51) Int. Cl.
*A61B 5/339* (2021.01)
*A61B 5/361* (2021.01)
*A61B 5/364* (2021.01)
*A61B 5/316* (2021.01)

(52) U.S. Cl.
CPC ............ *A61B 5/6852* (2013.01); *A61B 5/316* (2021.01); *A61B 2562/0214* (2013.01)

(58) Field of Classification Search
CPC ......... A61B 5/046; A61B 5/287; A61B 5/361; A61B 5/364; A61B 5/339; A61B 5/316; A61B 2562/0214
See application file for complete search history.

(56) References Cited

U.S. PATENT DOCUMENTS

| | | | | |
|---|---|---|---|---|
| 7,715,907 | B2 | 5/2010 | Koertge et al. | |
| 8,103,327 | B2 | 1/2012 | Harlev et al. | |
| 8,655,427 | B1* | 2/2014 | Greenspan | A61B 5/042 600/374 |
| 2002/0147445 | A1* | 10/2002 | Farley | A61B 18/1492 607/113 |
| 2008/0125772 | A1* | 5/2008 | Stone | A61M 25/10 606/41 |
| 2008/0214945 | A1* | 9/2008 | Koertge | A61B 5/046 600/515 |
| 2009/0024016 | A1* | 1/2009 | Zhang | A61B 5/01 600/381 |
| 2010/0168647 | A1 | 7/2010 | Tegg et al. | |
| 2011/0288605 | A1* | 11/2011 | Kaib | A61B 5/0006 607/5 |
| 2013/0123775 | A1* | 5/2013 | Grunewald | A61B 18/1492 606/41 |
| 2013/0296959 | A1* | 11/2013 | Milbocker | A61N 1/36592 607/17 |
| 2014/0200429 | A1* | 7/2014 | Spector | A61B 5/04017 600/374 |
| 2014/0378805 | A1* | 12/2014 | Ashton | A61B 5/04012 600/374 |

OTHER PUBLICATIONS

Calkins et al., 2012 HRS/EHRA/ECAS Expert Consensus Statement on Catheter and Surgical Ablation of Atrial Fibrillation: recommendations for patient selection, procedural techniques, patient management and follow-up, definitions, endpoints, and research trial design, Europace, 14(4):528-606 (2012).

HRS 2011: What's Hot, What's Not, in AF Ablation, Medtech Insight (Jun. 2011).

Jalife, Déjà vu in the theories of atrial fibrillation dynamics, Cardiovascular Res., 89(4):766-75 (2011).

Jamil-Copley et al., Novel technologies for mapping and ablation of complex arrhythmias, In: Breijo-Marquez (ed.), Cardiac Arrhythmias—New Considerations, Rijeka, Croatia: InTech (2012).

Knackstedt et al., Electro-anatomic mapping systems in arrhythmias, Europace, 10 Suppl 3:iii28-34 (2008).

LaPage et al., Update on rhythm mapping and catheter navigation, Curr. Opin. Cardiol., 26(2):79-85 (2011).

Liu et al., Three-dimensional imaging of ventricular activation and electrograms from intracavitary recordings, IEEE Trans. Biomed. Eng., 58(4):868-75 (2011).

Rabinovitch et al., Singular value decomposition of optically-mapped cardiac rotors and fibrillatory activity, J. Physics D: Appl. Phys., 48(9):095401 (2015).

Razminia et al., Nonfluoroscopic catheter ablation of cardiac arrhythmias in adults: feasibility, safety, and efficacy, J. Cardiovasc. Electrophysiol., 23(10):1078-86 (2012).

Tsuchiya, Three-dimensional mapping of cardiac arrhythmias—string of pearls—, Circ. J., 76(3):572-81 (2012).

Yamazaki et al., Heterogeneous atrial wall thickness and stretch promote scroll waves anchoring during atrial fibrillation, Cardiovasc. Res., 94(1):48-57 (2012).

Yamazaki et al., Pathophysiology of atrial fibrillation: From initiation to maintenance, J. Arrhythmia, 28:129-39 (2012).

* cited by examiner

Bandpass Filter 2-14 Hz

Modes 1-2 Filtered t = 505 ms

Y = 0

Y = 0.33

Y = 0.66

Y = 1

CATHETER AND METHOD TO LOCALIZE ECTOPIC AND REENTRANT ACTIVITY IN THE HEART

CROSS-REFERENCE TO RELATED APPLICATIONS

This application claims the benefit of U.S. Provisional Application Ser. No. 62/132,218, filed Mar. 12, 2015, entitled "A Catheter and Method to Localize Ectopic and Reentrant Activity in the Heart," the entirety of which is hereby incorporated herein by reference.

STATEMENT OF GOVERNMENT SUPPORT

This invention was made with government support under HL118304 awarded by the National Institutes of Health. The government has certain rights in the invention.

FIELD OF THE INVENTION

The present disclosure relates generally to identifying the heart arrhythmia in a subject and, more particularly, to developing ectopic and reentrant pattern mapping of the subject's heart rhythm using a catheter device.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Cardiac tachy-arrhythmias are caused by misfiring of electrical impulses known as action potentials and preclude the coordination of cardiac myocytes to effectively pump blood in its most severe form known as fibrillation. Electrophysiology studies are used to elucidate the mechanism of activation and resulting impulse propagation through cardiac tissue to identify specific patterns of sequential depolarization. This has enabled the recognition of rotors, macro or micro reentry (collectively referred to as rotors or reentrant activity), as well as automatic and/or triggered ectopic depolarization patterns as mechanisms that contribute to these arrhythmias.

In clinical electrophysiology, researchers have developed technology designed for the detection of electrical signals on the endocardial and epicardial surfaces of the heart, where cardiac mapping is used to localize in space and time the cardiac depolarization process.

Nonetheless, complex cardiac arrhythmias, such as atrial fibrillation (AF), atrial tachycardia (AT), and sustained ventricular tachycardia (VT) still present significant understanding and treatment challenges, especially given that anti-arrhythmic medications do not effectively control all the symptoms associated with these rhythm disorders.

AF, for example, is a chronic progressive disease that is caused by a complex interaction between initiating triggers and an abnormal substrate capable of sustaining the arrhythmia that may become permanent with time. AF itself causes electrical and structural remodeling of the atria, which in turn contribute to further the persistence of AF.

Paroxysmal AF is commonly treated with ablation that isolates pulmonary veins, but success rates of pulmonary veins isolation in patients with persistent AF is limited as electrical isolation of pulmonary vein foci is frequently insufficient. Additional linear ablation and/or ablation targeting complex fractionated atrial electrograms (CFAEs) are then often employed, which frequently result in the destruction of vast portions of the atria.

Intracardiac mapping has been used to guide catheter ablation procedures and position the ablation catheter within the anatomy of the heart chamber. Such intracardiac mapping creates 3D maps on the endocardial surfaces of the heart cavities in an attempt to identify the sources of abnormal rhythm targeted by ablation, and to reduce the reliance on fluoroscopy which is a radiation hazard for both patients and physicians.

Today in clinical practice the two most widely used electroanatomic mapping systems utilize catheter localization technology that is magnetic-based or impedance-based. Mapping systems can use multi-electrode grids either in contact or not in contact with the surfaces. The non-contact system consist of multi-electrode grid mounted on the surface of an insulating balloon creating an intracvitary volume conductor boundary. The contact mapping systems are more acceptable than the non-contact systems for diagnostic of arrhythmias, but none of the electroanatomic mapping system currently used in the clinic has been fully validated for mapping reentrant and ectopic activity during fibrillation There are several approaches to identify ablation targets for complex arrhythmias such as AF. Dominant frequency (DF) mapping identified self-organized high frequency vortex-like rotors that were proposed to be the drivers of AF. Rotors emit 2D spiral waves and 3D scroll waves that propagate through the heterogeneous cardiac muscle and interact with anatomic and functional obstacles, leading to wave front fragmentation and fibrillatory conduction.

Dominant frequency analysis has been used to show an evolution of mechanisms in AF patients, with pulmonary veins sources becoming less predominant as AF becomes more persistent and atrial remodeling progresses. This result agrees well with the relatively poor success rate of ablation in the pulmonary vein region in such patients. Paroxysmal AF was characterized by the hierarchical special distribution of dominant frequencies where the left atrium and pulmonary veins were always the fastest regions, while in persistent AF a more uniform distribution of higher dominant frequency values was observed, and the highest dominant frequencies were not found in the pulmonary vein region.

One of the major limitations of currently available ablation techniques is the difficulty of determining and visualizing electrical activity with sufficient sensitivity and specificity to accurately determine the location of potential sources of arrhythmia. Although the high-resolution method of optical imaging of electrical impulses can identify high frequency sources, it has not yet been developed for clinical use in patients.

SUMMARY OF THE INVENTION

Techniques are provided that identify and localize on to reentrant and ectopic patterns of electrical activation in the heart wall. These identified patterns correspond to atrial fibrillation, ventricular fibrillation, or other heart arrhythmia conditions and reflect patterns of fast and abnormal electrical activity. The techniques herein can detect remotely such patterns of the activation spread and lead efficiently an intra-cavitary catheter to the wall location where these pattern actually occur.

More specifically, the initial spreading site of the activity on any closed, but not electrically insulating, intra-cavitary surface is geometrically connected to the initial spreading site on the heart wall (i.e., ectopy) and is used as a remote guidance toward that ectopy. In addition, during reentrant activity in the cardiac walls, a filament, defined by the pivoting axis line of transmembrane or extracellular potentials, is extended into the volume conductor medium surrounding the muscle and is only interrupted at a non-conducting boundary. The filament in the heart cavity is thus also geometrically connected to rotors in the heart wall and is used as a remote guidance for the rotor. To facilitate the detection of the ectopies and filament in the cavity, a catheter probe assembly has been developed using what is called herein a "geodesic resistance" to detect these patterns and guide the catheter toward these patterns (i.e., reentrant and ectopic patterns of electrical activation spread) on the heart walls.

The catheter probe assembly employs "geodesic resistance" that, in analogy to an artificial attraction of electrical discharges in the atmosphere, creates the condition to detect electrical activity within the heart that is the result of centrifugal or rotating dipole sums corresponding to an ectopy or rotating cardiac action potentials in the heart wall, respectively.

The catheter probe includes a plurality of conducting poles positioned in a predetermined configuration relative to each other and functioning as either or both sensing and active poles. Each active pole is connected to a power supply that generates a coordinated time fixed or time varying potential to create a mono-polar or multi-polar (for example a dipole) source configuration inside the cavity. A high-input resistance detector is coupled to the catheter to monitor the voltage at the sensing poles and identify the particular space and time patterns of the potentials in the heart cavity that are the summed contribution of the heart sources and the active pole sources. Specifically in an example shown below, when a rotating dipole is generated in the active poles, its filament merges with the filament of the heart reentrant activity and a geometrical connection exists between the catheter and the pivoting point of the reentrant activity on the cardiac wall. Depending on the time and space patterns of potentials generated on the active poles, the geometrical localization of reentrant and ectopic activities that drive the arrhythmia are accomplished.

To characterize features of the cardiac electrical activity during arrhythmia across the entire heart, existing cardiac mapping technologies rely on either low resolution multi-electrode grids spread over the entire internal walls of the heart cavities or on the body surface, or rely on roving the internal walls with a relatively small-area higher-density multi-electrode grids, which span over only a small region of the heart at a time. While the former method provides a low-resolution panoramic mapping, the latter provides a higher resolution but requires sequential recordings to cover the whole cardiac area. In addition, both of these two mapping approaches depend heavily on the quality of the electrode-tissue (heart surface or body surface) contact and are not validated for detection of ectopies and/or reentrant electrical activation patterns.

The present techniques includes examples that achieve the advantages of each of those approaches, but in a single method and device. The intracavity mapping device gives a panoramic mapping capability that in contrast to existing approaches that depend heavily on electrode-surface contact quality is designed to be totally independent of such contact and is designed to detect specifically the patterns of activity that are the sources of the arrhythmia. To achieve the needed accuracy in localizing the arrhythmia sources, the invented system is designed to be directed to move inside the cavity toward the arrhythmia source, without spending unnecessarily time roving areas that are not critical to arrhythmia maintenance as is the case in the existing roving high-density small area mapping approaches.

In accordance with an example, a catheter comprises: a housing extending from a proximal end to a distal end configured for insertion into target region of a subject, the housing having an inner wall; and a plurality of electrodes positioned within the housing and spaced apart from one another, the electrodes extending from the proximal end to the distal end, each electrode providing an electrical conduction path from the distal end in the target region to the proximal end, and wherein the plurality of electrodes are positioned such that collectively the electrodes provide electrical conduction paths over a region of the target region, and wherein the catheter is configured to maintain spacing distance between the plurality of electrodes during deployment of the catheter within the subject.

In accordance with another example, a system for mapping electrical cardiac activity, the system comprises: a catheter comprising, a housing extending from a proximal end to a distal end configured for insertion into target region of a subject, the housing having an inner wall; a plurality of electrodes positioned within the housing and spaced apart from one another, the electrodes extending from the proximal end to the distal end and terminating at different locations around the periphery of the housing, each electrode providing an electrical conduction path from the distal end in the target region to the proximal end, and wherein the plurality of electrodes are positioned such that collectively the electrodes provide electrical conduction paths over a region of the target region, and wherein the catheter is configured to maintain spacing distance between the plurality of electrodes during deployment of the catheter within the subject; one or more processors coupled to the plurality of electrodes of the catheter; and one or more non-transitory computer readable memories coupled to the one or more processors, wherein the one or more memories include computer-executable instructions stored therein that, when executed by the one or more processors, cause the one or more processors to, receive electrical signal data from at least some of the plurality of electrodes of the catheter, identify electrical signal nodes in the received electrical signal data, develop a cubic phase map from the electrical signal data, wherein the cubic phase map includes an indication of the identified electrical signal nodes, and display the cubic phase map.

In accordance with another example, a method for detecting a filament causing arrhythmia in a heart of a subject, the method comprises: receiving, at one or more processors, electrical signal data from a plurality of electrodes disposed within a catheter; filtering, in the one or more processors, the electrical signal data; linearly interpolating, in the one or more processors, the electrical signal data, based on the source electrode or electrodes producing the electrical signal data; applying, in the one or more processors, phase transformation to electrical signal data and developing a cubic phase map of the transformed electrical signal data; identifying, in the one or more processors, with the cubic phase map one or more singularity points each indicating a filament of electrical activity in the heart.

In accordance with yet another example, a method for detecting an ectopy causing arrhythmia in a heart of a subject, the method comprises: receiving, at one or more processors, electrical signal data from a plurality of electrodes disposed within a catheter; filtering, in the one or more processors, the electrical signal data; linearly interpolating, in the one or more processors, the electrical signal data, based on the source electrode or electrodes producing the electrical signal data; applying, in the one or more processors, phase transformation to electrical signal data and developing a cubic phase map of the transformed electrical signal data; and identifying, in the one or more processors, with the cubic phase map one or initial activation points each indicating an ectopy of electrical activity in the heart.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 2A illustrates the original, unprocessed electrical signals (the raw electrical signals). FIG. 2B illustrates these electrical signals after a bandpass filtering.

FIG. 3A shows plots of cubic phase spaces and showing two (2) phase convergence points (also termed "singularity points" or "SP") corresponding to the filament at the center of a passive rotor inside the atrial cavity. FIG. 3B illustrates sections of the phases as measured across the mid main planes of the cubic data.

FIG. 7B illustrates the electrical signal data after a bandpass filtering has been applied.

DETAILED DESCRIPTION

Figure 1A:
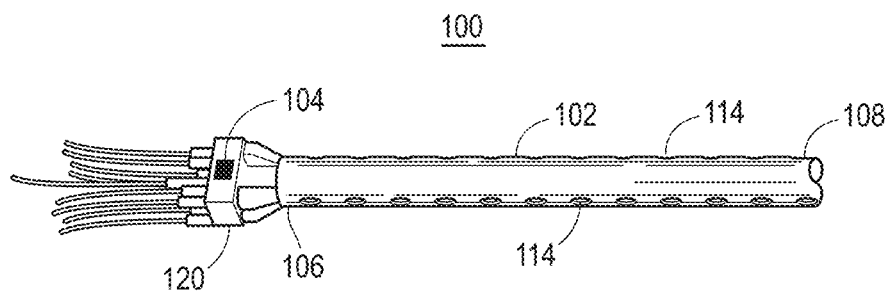
FIGS. 1A and 1B illustrate a catheter device in accordance with an example herein, in particular a catheter having eight (8) outer electrodes, serving as sensing electrodes, and with a separate high conductance pole electrode, serving as an active electrode, in a central region. The active electrode may be connected to either an external ground or a power supply with a closing circuit to the cavity itself. The catheter includes fluid channels for permitting fluid access in the inner catheter region where the active electrodes are located.
Figure 1B:
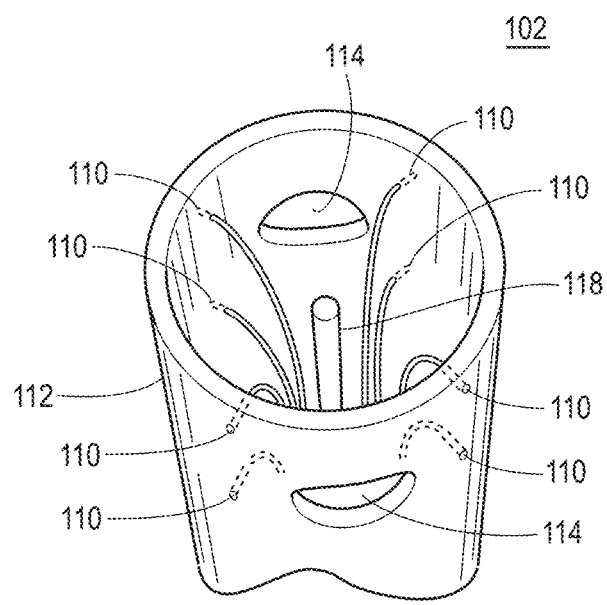

FIG. 1A illustrates an electrical activity catheter analysis system 100, having a deployable catheter 102 coupled to an electrical activity processing device 104. The catheter 102 (FIG. 1B) provides a geodesic pathway for capture and conduction of electrical activity through the catheter 102 into the electrical activity processing device 104. While the illustrated examples are described as providing a geodesic capture region (e.g., capture around the cylindrical outer surface of the catheter 102), electrical activity may be detected at any of number of simultaneous, multiple points in the heart wall using catheters in accordance with examples herein.

In the illustrated example, the catheter 102 includes a proximal end 106 coupled to the device 104 and a distal end 108 deployable with a heart chamber, whether atrium or ventricle to analyze electrical activity. The catheter 102 includes a plurality of electrodes (also termed "poles" herein) 110 that extend along a length of the catheter from at or near the proximal end 106 to the distal end 108 to provide a conduction path to the electrical activity device 104. The electrodes 110 travel along the shaft of the catheter 102 until that distal end 108, where the electrodes 110 bend outwardly to form the end points (or corners or tips) of, for example, a cubic space, i.e., the 8 corners of a cube. In the illustrated example, the catheter 102 includes eight (8) electrodes 110 which correspond to 8 vertices of a phase volume cubic space that is constructed by the device 104. However, more or fewer electrode poles may be used, as desired. For example, 4 electrodes forming a tetrahedron could be used to form the coordinal mappings described herein. These electrodes 110 serve as sensing electrodes sense electrical potentials in the heart cavity.

The geometrical configuration of the sensing and active electrode need not be fixed during all times; the inter-electrode distances need to be steady only during the acquisition of signals. In particular it is understood that the catheter is inserted into the patient heart cavity with all its electrodes occupying a narrow and small volume that permits its insertion into the heart through blood vessels. Once inside the cavity, the catheter is deployed to its predesigned geometrical configuration that occupies a larger volume of about 1 cm$^3$. After usage, the catheter will be shrunken to permit its removal from the heart and the patient body.

In some examples, the electrodes 110 are spaced evenly around a circumference of the catheter 102 on an outer insulated housing 112 to provide an full circumference (full volume) detection of electrical activity within the heart chamber, without having to move the catheter around. The space between the electrodes 110 may be empty and free to contain a volume conductor within the catheter 102. For example, in in vivo deployment, the catheter may be sized for blood flow through one or more openings 114 in the catheter 102 that provide inlet/outlet flow of a fluid. In this way, conduction within the volume of the catheter may be achieved, but allowing fluid with an amount of conductivity to fill the space between electrodes 110. For example, in isolated heart experiments, a specific conductive fluid may be inserted into the catheter 102 to increase conduction of the electrodes 110.

The electrodes 110 have distal tips that may be floating or fixed in place relative to the wall of the catheter. The electrodes 110, as discussed, may operate as "active" or "sensing" electrodes, or in some examples as dual mode electrodes that both apply a stimulation single and sense for responses in the sample.

The electrodes 110 may be coated conducting wires formed of Au, Ag, etc., or any other suitable conducting medium. The wires may be circular in cross section, square in cross section, rectangular in cross section, or take on other multi-sided geometries.

Along with the electrodes 110, in the example of FIG. 1, the catheter 102 includes a high conductance central pole electrode 118 (termed an "HCP" or "HCP" electrode) positioned between the poles 110. The central pole is an active pole, receiving an electrical signal that is applied from within the catheter to provide a biasing electrical signal, reference scan electrical signal and to provide balancing. The central pole 118 may be positioned equidistant from the poles 110, for example. The electrode 118 may be grounded separately from the electrodes 110 to provide a different circuit path for electrical signals. In this way, the grounding and voltage biasing of the electrode 118 may be controlled separately from the electrodes 110. More generally, it has been found, that the electrode 118 provides an electrical signal balancing on the data collected and analyzed by the processing device 104.

Figure 17:
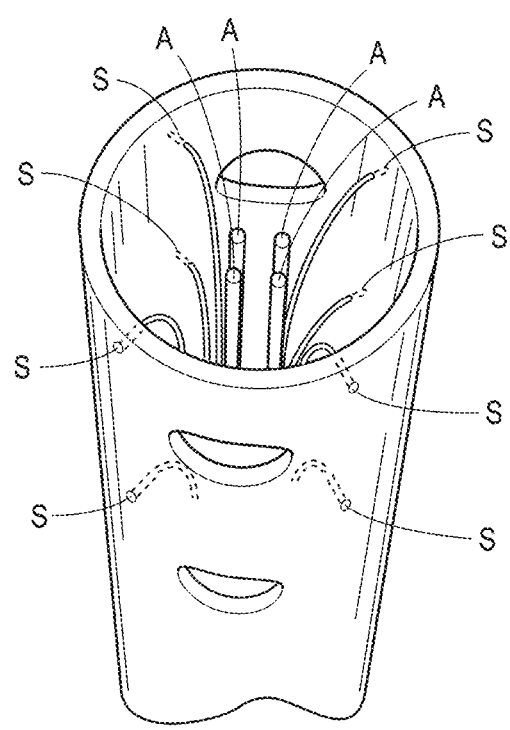
FIG. 17 illustrates a catheter device in accordance with another example having a plurality of active electrodes (A) interiorly positioned relative to a plurality of outer sensing (S) electrodes.

In other examples, including for example the device in FIG. 17, the active HCP electrode is replaced by a plurality of fixed active electrodes positioned either interstitially between the outer (sensing) electrodes or centrally within the catheter.

In the illustrated example, the processing device 104 is coupled to the catheter 102 through an interface module 120, which may include a catheter connector assembly connecting each of the electrodes 110 and 118 to the processing device 104. In some examples, the interface module 120 provides only electrical connection to the device 104. In other examples, initial signal processing may be done to the processing device 104, such as bandpass filtering, signal gain control, and/or analog to digital conversion.

Example 1

Figure 2A:
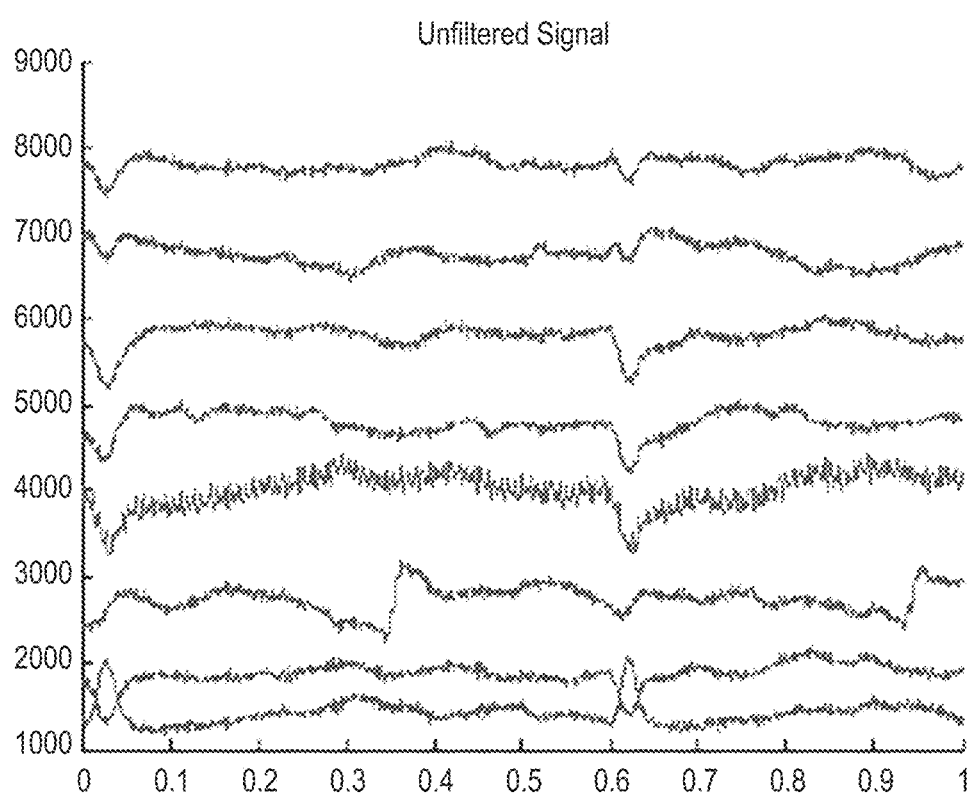
FIGS. 2A and 2B illustrate two plots of voltage signal measured from the outer, sensing electrodes of FIGS. 1A and 1B, over a time series obtained inside the left atrium cavity. The active, central electrode was held at 0V difference with the heart, which served as ground.

In an example implementation, a catheter, e.g., catheter 102, was inserted into a solution-filled cavity of the left atrium (LA; no contact with the walls) of a sheep experience atrial fibrillation (AF). Electrical signal data was collected and recorded, specifically voltage time series data, at each of the 8 outer electrodes functioning as unipolar electrodes. A common reference signal was constructed from joining 4 (or 3; depending on availability), of opposing electrodes, i.e., vortices, through a high resistance connection (i.e., a local Wilson central terminal configuration). FIG. 2A shows sample data collected in the 8 vortices electrodes during AF in the sheep with a central HCP electrode maintained at a 0V difference with the grounded heart, i.e., short circuited with the heart. In the example shown in FIG. 2B, filtering is done on the electrical signal data, by a processing device. For example, the original data was passed through a bandpass filter and filtered at 1-20 Hz band, thus providing a low pass filtering. Following the bandpass filtering, the electrical data from the 8 vortices electrodes was linearly interpolated in the space between the vortices; and then phase analysis was performed by the use of the Hilbert transform.

Figure 2B:
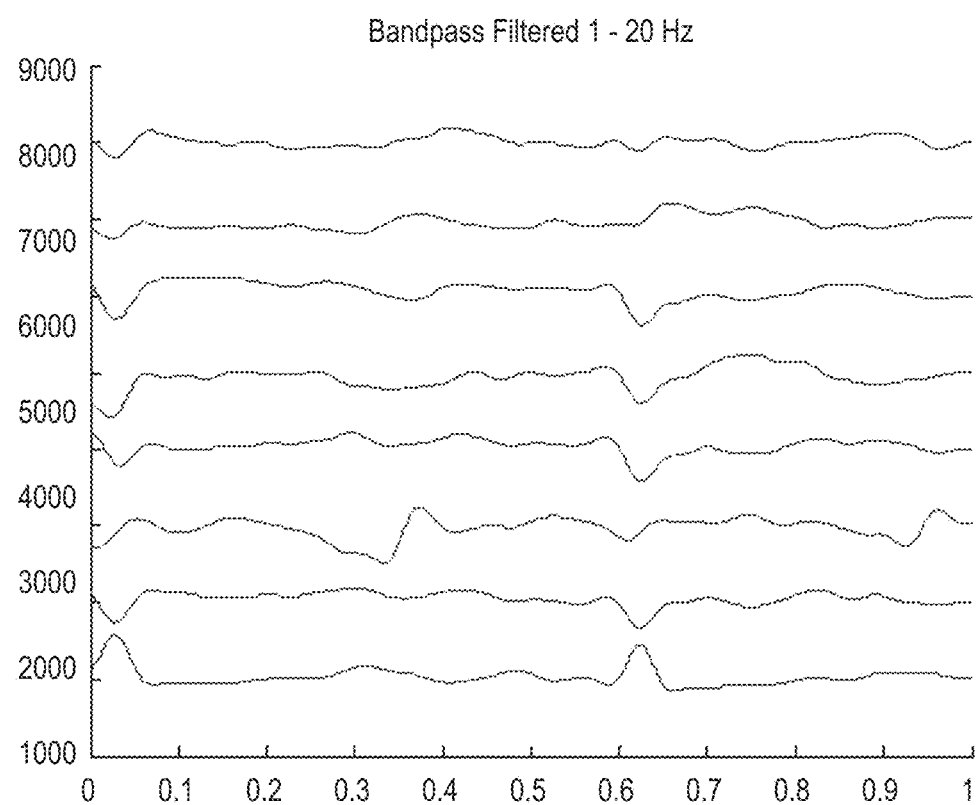
Figure 3A:
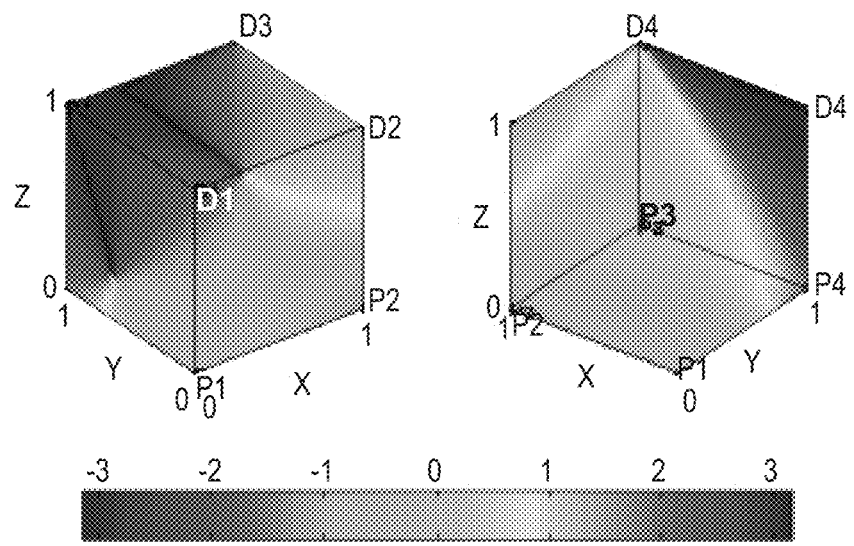
FIGS. 3A and 3B illustrates phase data processed from the electrical (voltage) signals from FIGS. 2A and 2B.
Figure 3B:
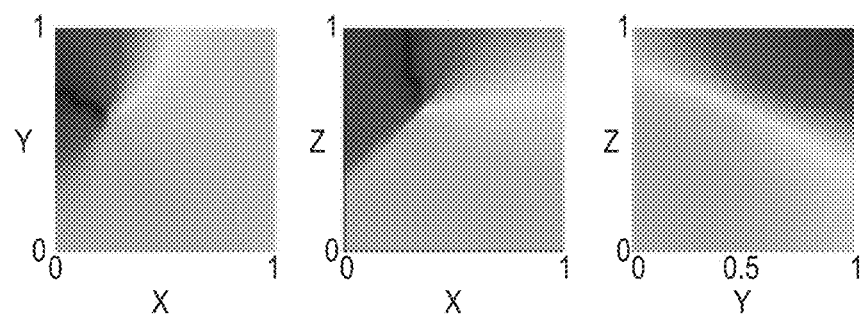

FIGS. 3A and 3B show the analysis of the data in FIGS. 2A and 2B. The result is a cubic phase space, shown from two different angles (FIG. 3A) and from three sections through the middle of the three main planes of the cubic space (FIG. 3B). The phase data is shade-coded to correspond to the phase of the action potentials (blue 250 to yellow 252 to red 254; from $-\pi$ to $\pi$).

Figure 4:
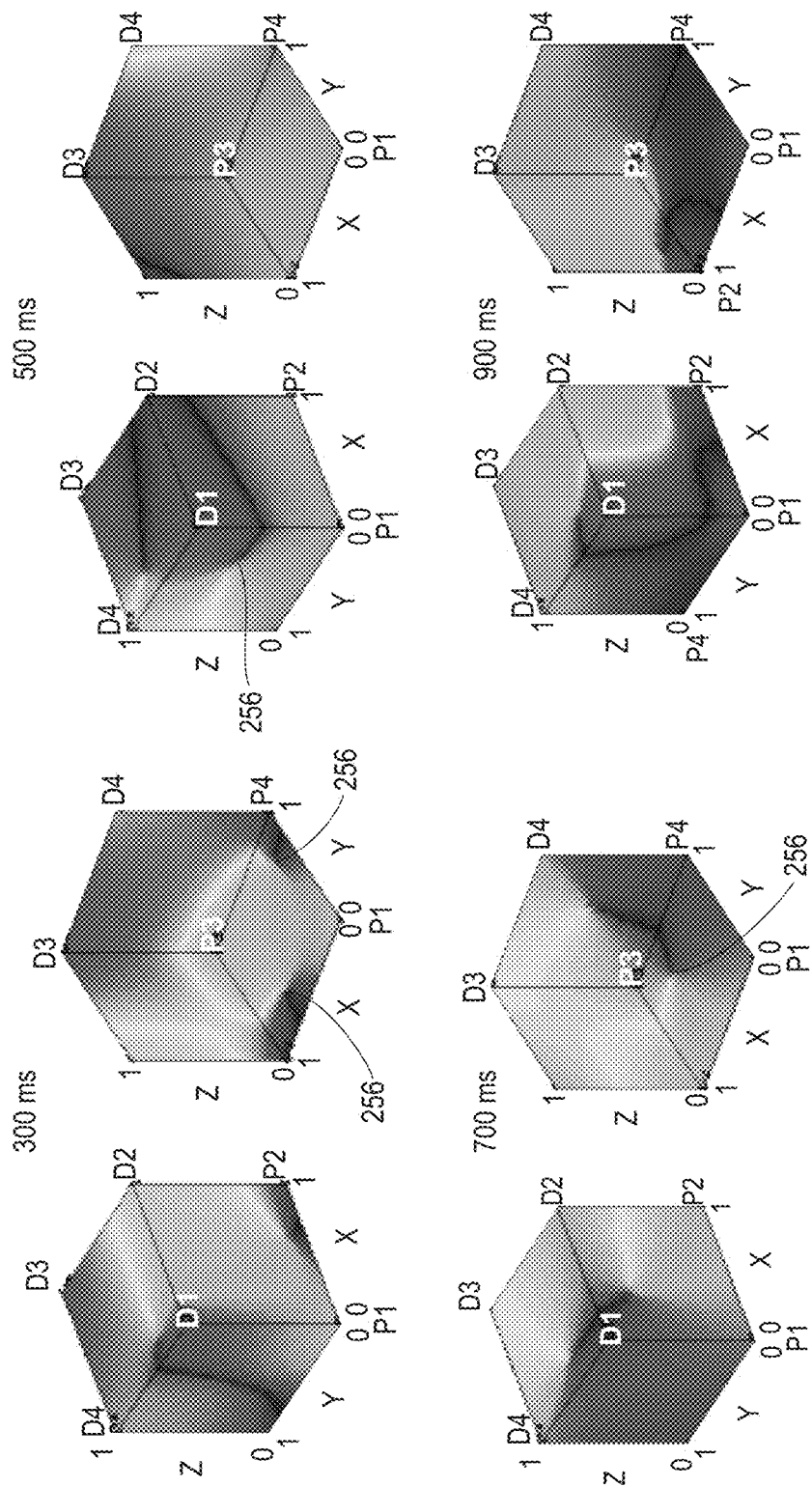
FIG. 4 illustrates cubic phase plots of time-based change in the SP as detected by the catheter of FIGS. 1A and 1B inside the atrial cavity. Shown are two different views of the interpolated phase data on the cube faces at four different times during AF signals are shown. The central electrode was maintained at 0 Volts. There is continuous presence of an SP on the distal face, i.e., the plane perpendicular to the central electrode (maintained at 0 Volts). The couple of pair of SPs on the panels at 300 ms and 700 ms demonstrate the existence of two filaments crossing the cube space.
Figure 5:
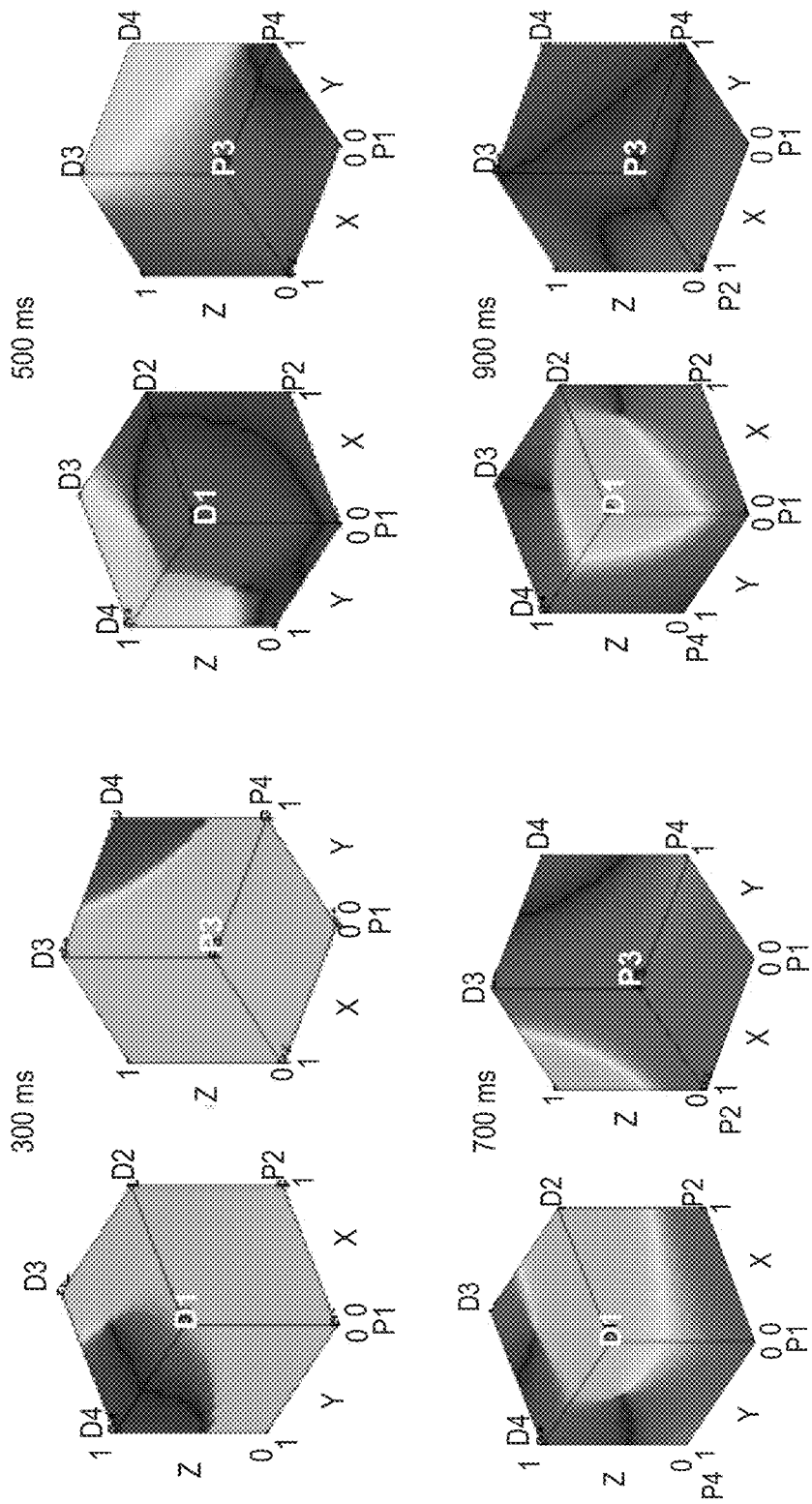
FIG. 5 illustrates cubic phase plots of time-based change in the SPs as detected by the catheter of FIGS. 1A and 1B, where the central electrode is maintained at 7 Volts relative to the grounded heart. Two different views of the interpolated phase data on the cube faces at four different times during VF signals are shown.

From analyzing the phase image data of FIGS. 3A and 3B, rotational activity is visible. This activity corresponds to the passive rotational activity of the potential in the cavity, where the medium is not excitable but it is dependent on the electrical activity in the surrounding atrial walls of excitable medium. FIGS. 4 and 5 illustrate plots of further cubic phase data showing the time course of the linearly interpolated phases of the cube's inner-space in various times during the VF. For example, FIG. 4 presents data from signals already analyzed, as shown in FIGS. 2 and 3. FIG. 4 illustrates several singularity points (SPs) 256 that suggests the presence of filaments and pivoting of the local electrical potential distribution during AF in the passive volume conductor, which is the cavity of the LA (left atrium). In FIG. 4, the HCP electrode was maintained at 0V difference with the heart (serving as ground). We observed that, in addition to a relatively steady SP at the distal face, another filament was transiently presented at around 300 and 700 ms. In contrast, FIG. 5 illustrates a similar analysis to that of FIG. 4, but with the HCP electrode maintained at a 7V difference with the grounded heart. In this example, only one filament is present with a steady phase singularity point (SP) at the distal face. No additional transient filament was present. In these examples, the HCP, as an active electrode, is able to attract the filament within the heart walls, as that filament moves from SP point to SP or from SP to one of the sensing electrodes.

Thus with the catheter device having an internal active electrode, such as the HCP electrode, surrounded by a plurality of fixed sensing electrodes, the stability of the singularity points (SPs) is increased, thereby making the exact location of each SP easier to determine, with less transient movement in SPs over multiple detection cycles. The central HCP electrode provides a least resistance path for currents and as such provides an anchoring location, in particular for a filament that has its endocardial end at a rotor. In this way, the processing device controlling the operation of the catheter can use the HCP electrode to provide at any location within the heart cavity the SPs and filament which are necessary for efficient roving the heart cavity toward the rotors on the endocardium that may drive the AF.

It is noted that while the examples of FIGS. 3A, 3B, 4, and 5 are discussed in reference to cubic phase spaces and using outer sensing electrodes and one central active electrode, other electrode configurations may be used. An example is shown in FIG. 17 below. In some examples, the outer electrodes include both active electrodes and sensing electrodes, in an alternating pattern around the inner wall of the catheter. Beyond the electrodes, other 3 dimensional geometries may be used as well to determine SP points. Other configurations include, by way of example, electrodes arranged on the surface of a sphere, or on the vortices of a tetrahedron, with resulting phase spaces.

Figure 6:
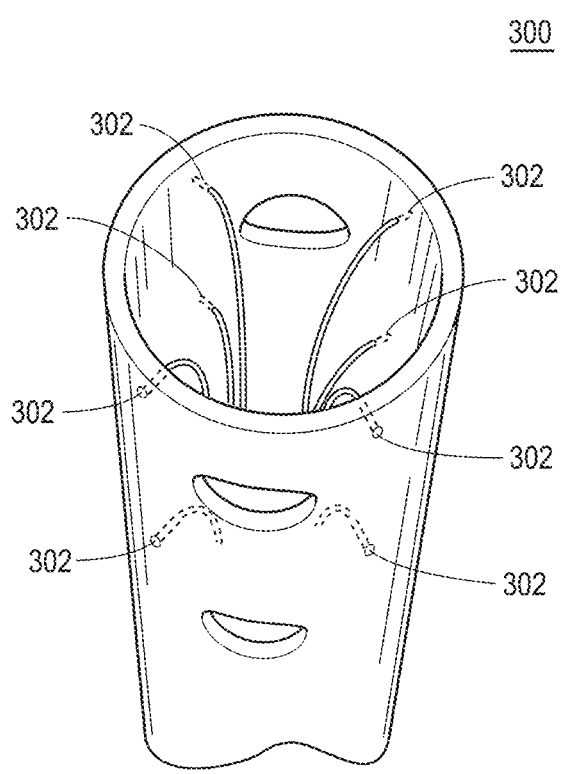
FIG. 6 illustrates a catheter according to another example and having a plurality of sensing electrodes but no central electrode.

While the catheter 102 illustrates a central electrode (e.g., the HCP electrode 118), catheters may be implemented without the central electrode, such as catheter 300 in FIG. 6, which includes a plurality of outer electrodes 302, but which does not include an HCP electrode.

Example 2

In an example implementation of a catheter like that of catheter 300, cardiac extracellular electrical activity was recorded at 8 electrodes, for 8 vertices of a cube. In this example, the edge length of that cube was 1 cm. The spacing distance is determined from the size of the catheter. As with the catheter 102, the catheter 300 the space between the vertices electrodes is empty and free to contain the volume conductor.

Figure 7A:
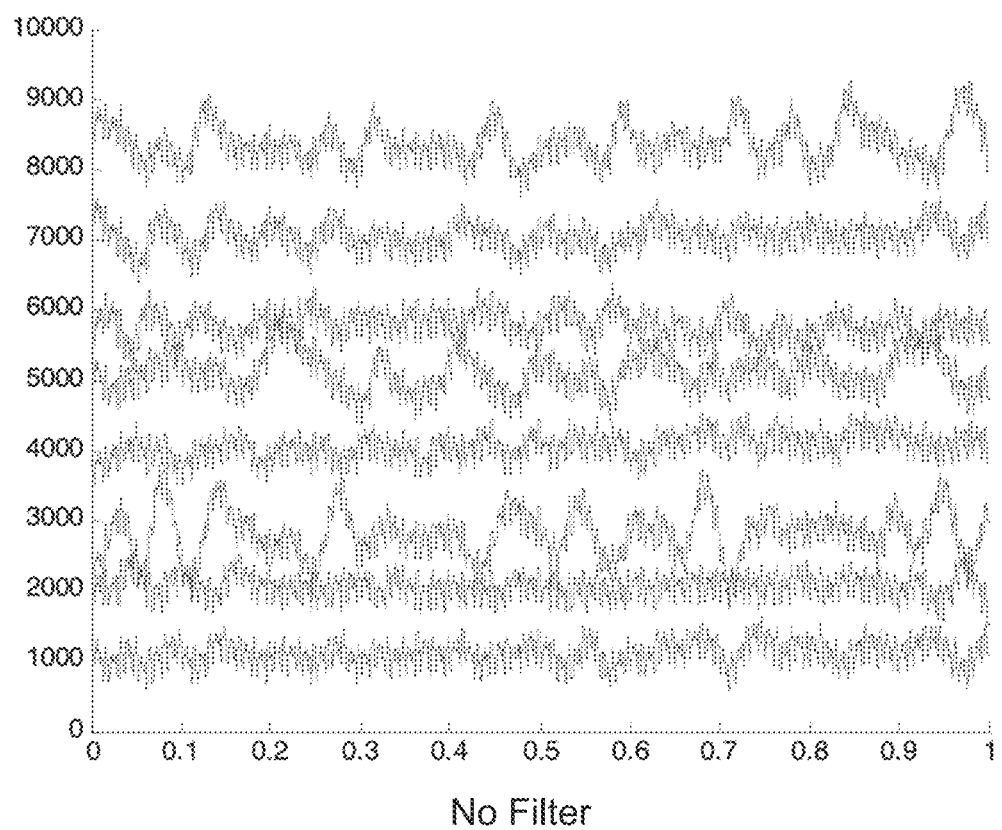
FIGS. 7A and 7B illustrate a plot of electrical signal data (i.e., voltage) over 1-sec long time series sampling window from each of the eight electrodes, taken from the left atrium of a sheep during atrial fibrillation, for a catheter having the configuration of FIG. 6.
Figure 7B:
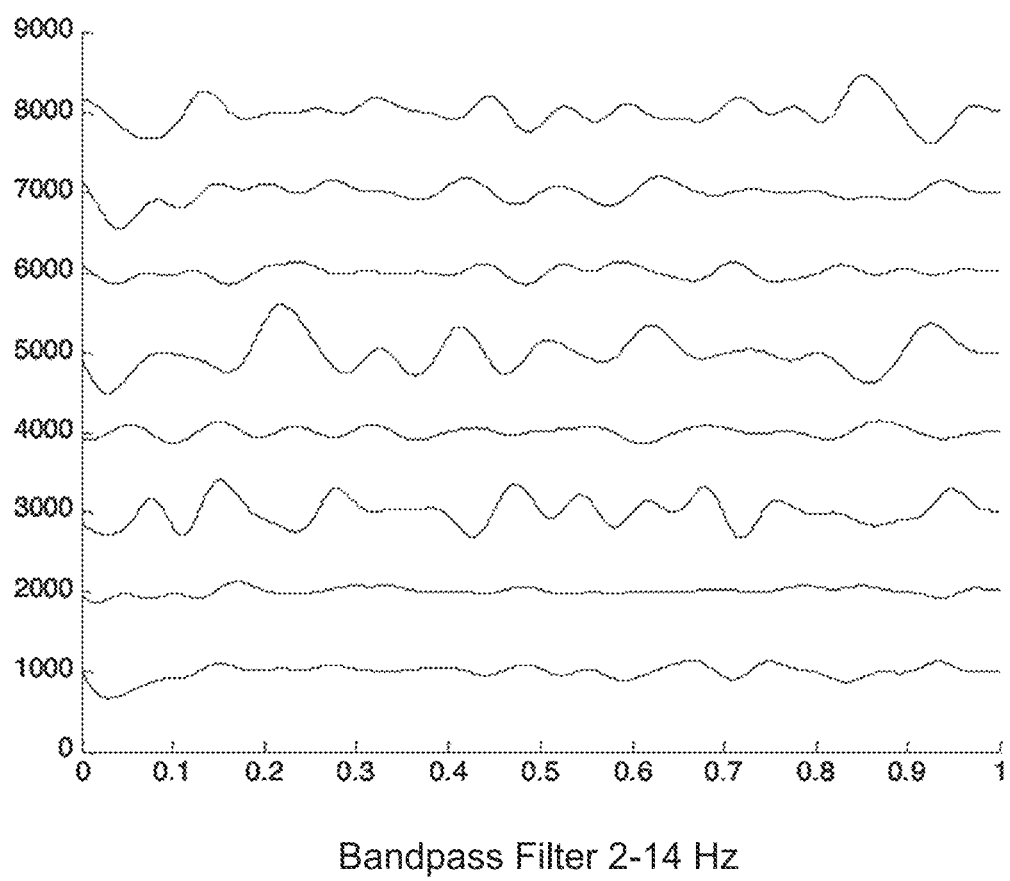

In an example implementation, data was acquired from by inserting the catheter into a solution-filled cavity of the left atrium ("LA"; no contact with the walls) of a sheep during pacing sinus rhythm and atrial fibrillation, similar to that of Example 1 above. Voltage time series were recorded at each of the 8 electrodes 302 as unipolars with a common reference signal constructed from joining 4 (or 3; depending on availability), of opposing vortices through a high resistance connection, e.g., like a Wilson terminal. FIG. 7 shows sample data collected during atrial fibrillation in the sheep, where the original data was bandpass filtered at 2-14 Hz band. Following the bandpass filtering the data from the 8 vortices 302 was linearly interpolated in the space between the vortices and then phase analysis was performed by the use of the Hilbert transform, resulting in the cubic phase plot of FIG. 8A which shows the resulting phase cube from 3 different angles, and the plot of FIG. 8B which shows sections through the 3 main planes of the corresponding cubes of FIG. 8A.

Figure 8:
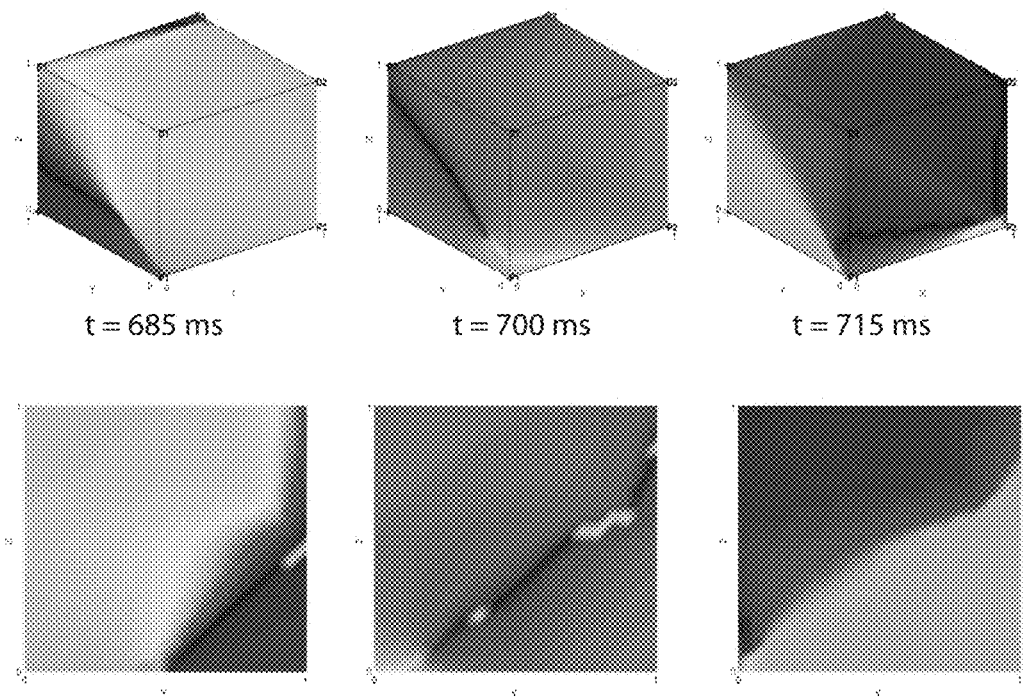
FIG. 8 illustrates cubic phase data for the interpolated data points in the cubic space between the eight electrodes for the catheter in FIG. 6. The panels show phase convergence points corresponding to the a filament at the center of passive rotor (the space is a passive and not an excitable medium) crossing the cube space.
Figure 9A:
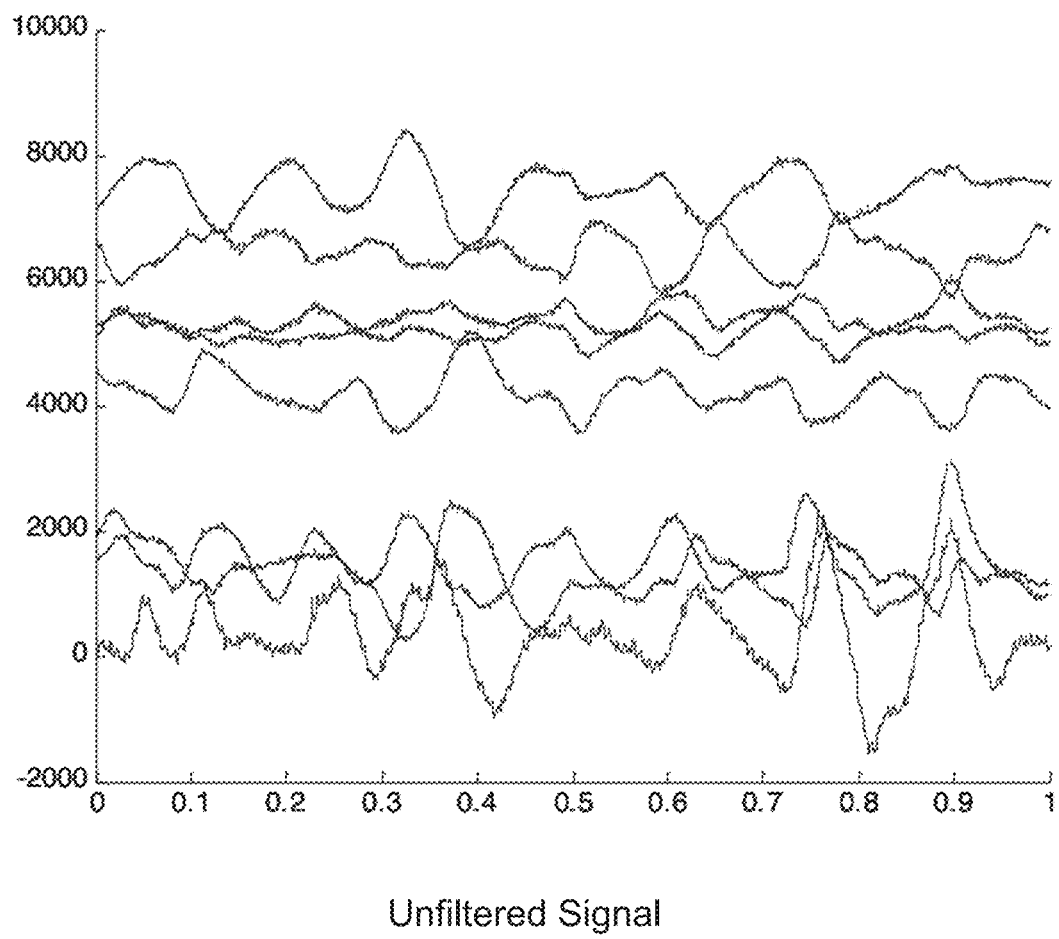
FIG. 9A is a plot of electrical signal (voltage) data for 1-sec long time series sampling window obtained with the eight electrodes of the catheter inside the left atrium cavity during atrial fibrillation in sheep, for a catheter having the configuration of FIG. 6.
Figure 9B:
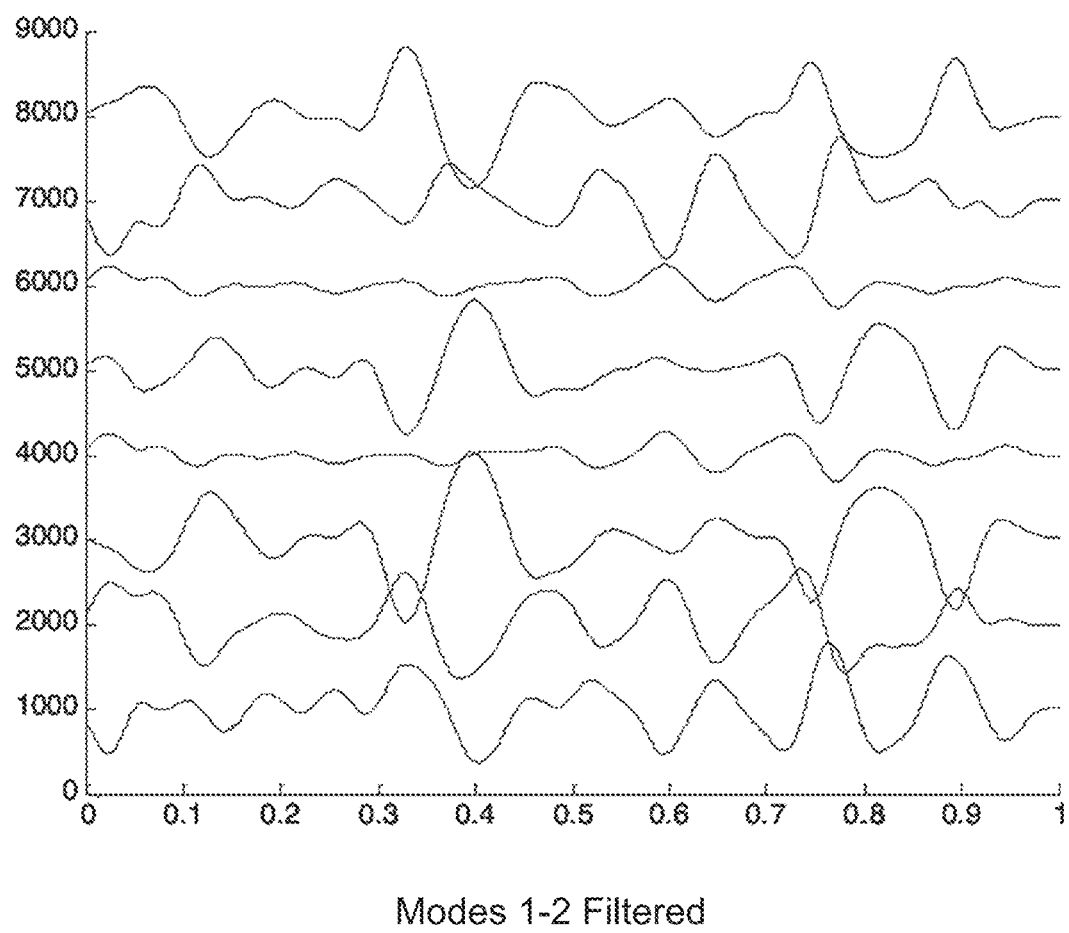
FIG. 9B is plot of the electrical signal data showing the 1st and 2nd mode of the signal data after singular value decomposition and reconstruction (SVD/R) has been performed.
Figure 10:
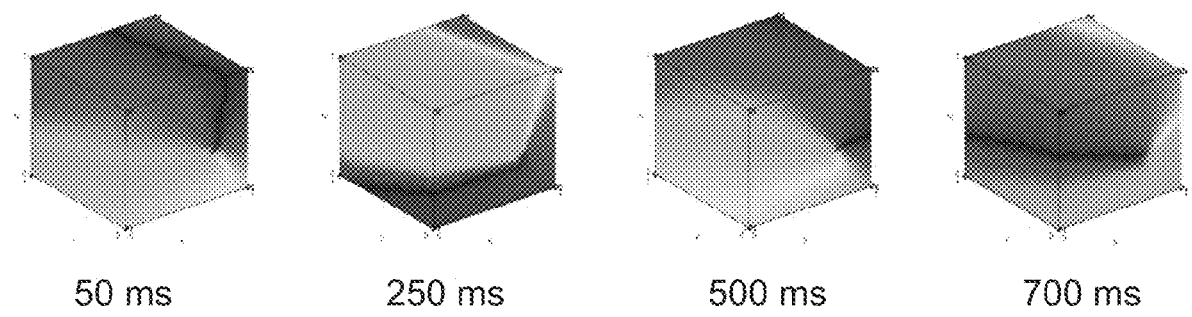
FIG. 10 illustrates cubic phase spaces calculated for the interpolated data points in the cubic space between the eight electrodes after the SVD/R of FIG. 9B. When only modes 1 and 2 are used, a stationary rotating activity (SPs) is present throughout the entire duration of AF.
Figure 11:
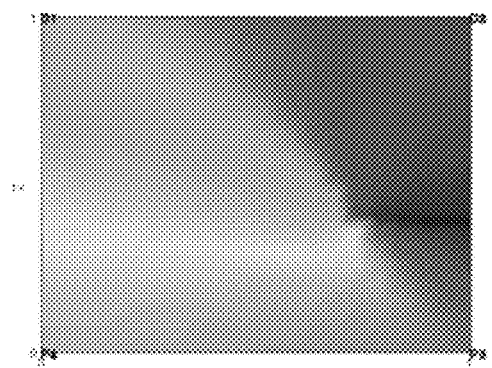
FIG. 11. is a plot of phases in plane sections of the cube space showing a singularity point running continuously through the cube in the XZ plane from one face (y=0) to the contralateral face (y=1 cm) for the cubic phase data of FIG. 10.
Figure 11:
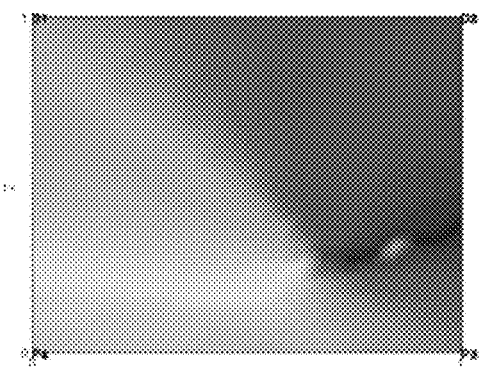
Figure 11:
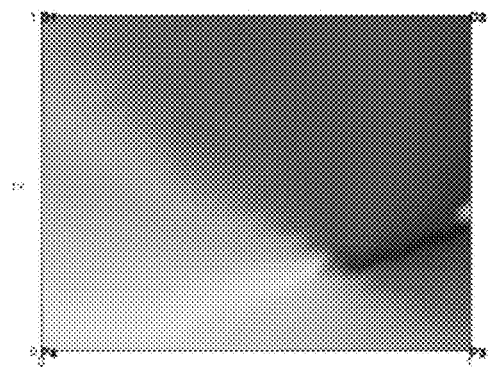
Figure 11:
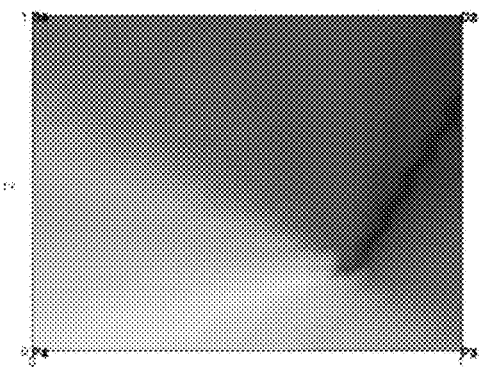

An alternative filtering approach was also demonstrated in an example by the use of the singular value decomposition and reconstruction (SVD/R) on the electrical signal data. In FIG. 9A, the 8 unprocessed traces of voltage time series (i.e., signals from each of the outer electrodes 302) is shown. FIG. 9B illustrates the resulting electrical signal after the processing device applies an SVD processing to each of the traces, and where data based solely on the 1st and 2nd SVD modes were reconstructed. The effect of the reconstruction of the data with only its highest modes is equivalent to filtering out the least important spatio-temporal features of the activity, without any pre-assumption of their spectral content. FIGS. 10 and 11 illustrate the linear interpolation of the phases of the 8 traces in the cube's inner-space at different times. Contrary to the phases obtained with the bandpass filtering as shown in FIG. 8A, FIG. 10 shows a steady singularity point that suggests the presence of stationary pivoting of the local electrical potential distribution during AF in the passive volume conductor, which is the cavity of the LA. FIG. 11 further demonstrates that the collection of the phase singularity points (SPs) at adjacent planes inside the cube form a continuous filament.

That is, the SVD processing has been shown to create stability of the singularity points (SP). The SVD processing provides such benefits, at least in part, because as the filament inside the cavity is continuous, the filament must span the entire cavity, between 2 points on the endocardial wall of the atria. Thus, applying a filtering that will bring about the most important modes of activity, either by the bandpass filtering at a particular band (e.g., including the highest dominant frequency of the AF) or by the SVD/R approach, we reveal inside the cavity the filament that when traced toward the wall will lead to the region that contains the driving rotor of the AF.

Figure 12:
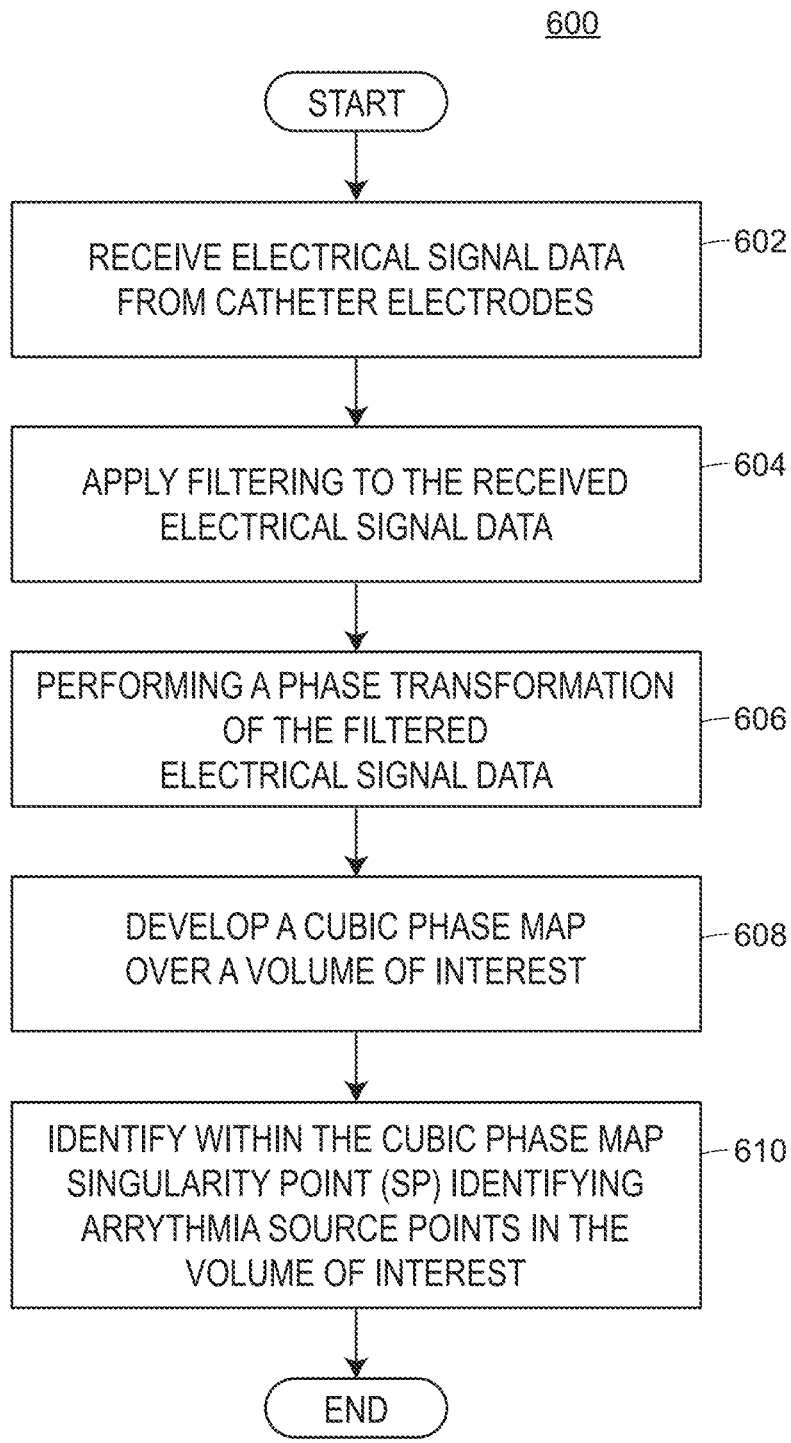
FIG. 12 illustrates an example process for detecting a filament causing arrhythmia in a heart.

FIG. 12 illustrates an example process 600 for detecting a filament causing arrhythmia in a heart, as may be implemented by the processing device 104 coupled to one of the catheters 102 or 300. The processing device receives electrical signal from the catheter electrodes (602), for example, from the sensing electrodes. The received electrical signal is filtered and interpolated by the processing device (604), after which a phase transformation is performed on the filtered electrical signal (606), more specifically, to the data within the filtered electrical signal. The processing device then develops a cubic phase map over a volume of interest for the sample under examination (608). In some examples, the processing device will determine, during assessment, what that volume of interest is. In other examples, the volume of interest may be predetermined. With the cubic phase map formed, the processing device will identify singularity points within the cubic phase map (610). These are the guiding points toward sources for arrhythmia in walls of the cardiac volume of interest, or at least candidate locations of the source of arrhythmia. The identified points, for example, may be used as treatment points of an arrhythmia treatment, such as ablation techniques, etc.

Figure 20:
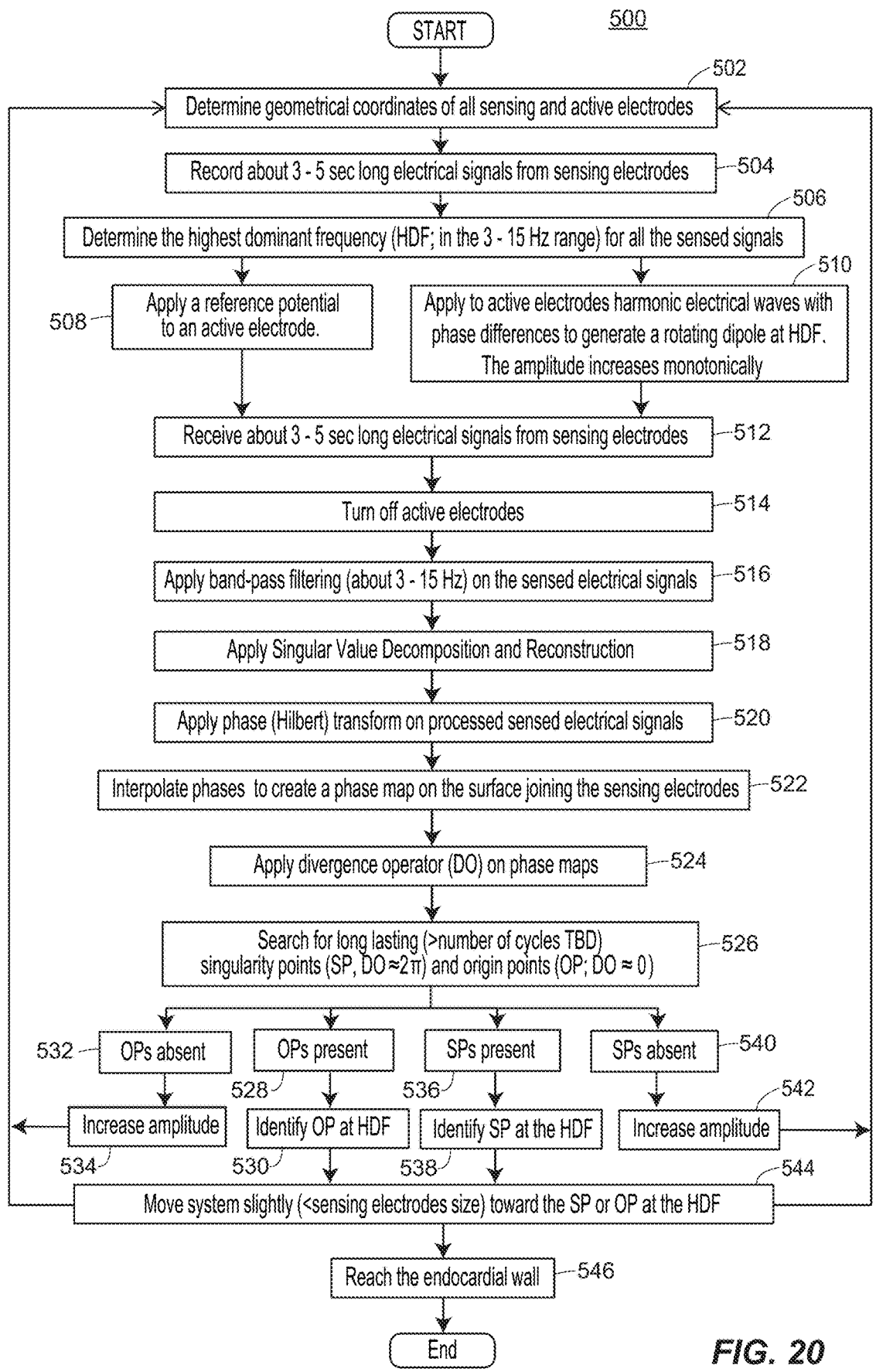
FIG. 20 is a flow diagram of an example implementation of a process for identifying arrhythmia sources.

FIG. 20 illustrates a detailed example implementation of a process 500 for identifying arrhythmia, similar to that of FIG. 12, and as may be performed for a processing device as described herein. The geometric coordinates of the sensing electrodes and active electrodes are obtained (502), for example, from data on the geometry of a catheter, or from real time measurement techniques, such as real-time catheter location measurement techniques. Over a sampling window of time, e.g., 3-5 s, the processing device will collect the electrical signals from the sensing electrodes (504). From here, the highest dominant frequency (HDF in the range of 3-15 Hz) is determined for all the sensed signals (506). This provides initial signal data.

Figure 14:
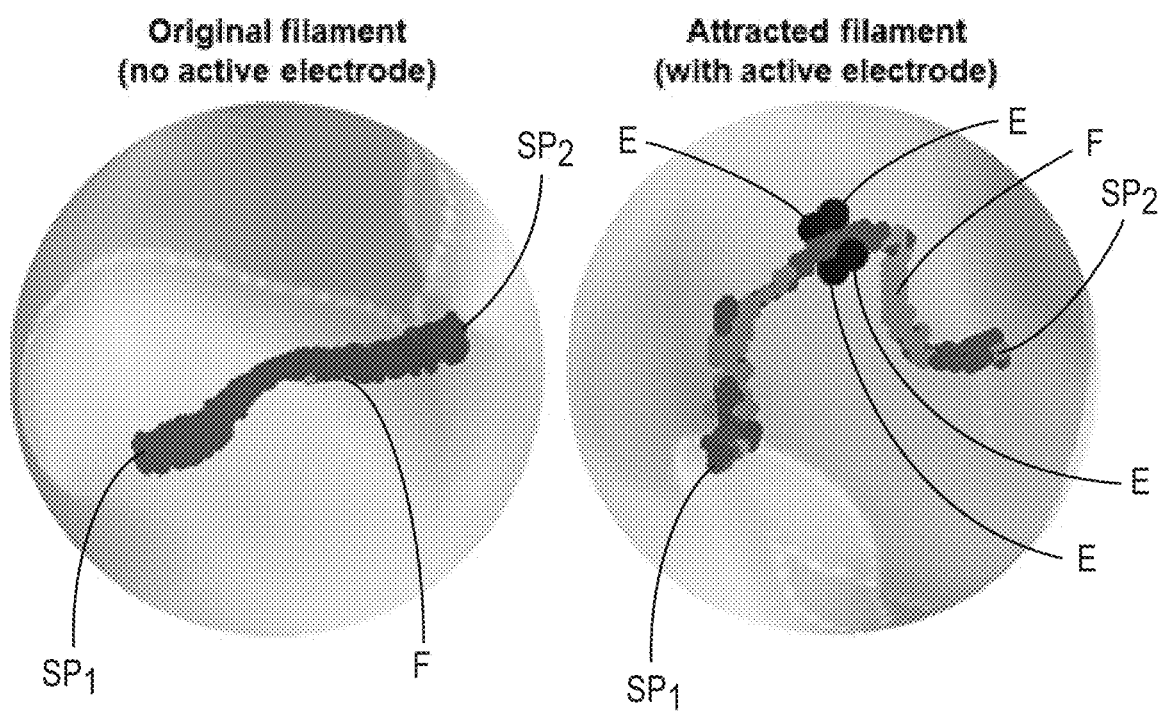
FIG. 14 illustrates filaments formed between phase singularity points and showing the effect of a catheter having multiple active electrodes creating a rotating dipole altering the filament shape to cross the cube space.
Figure 15:
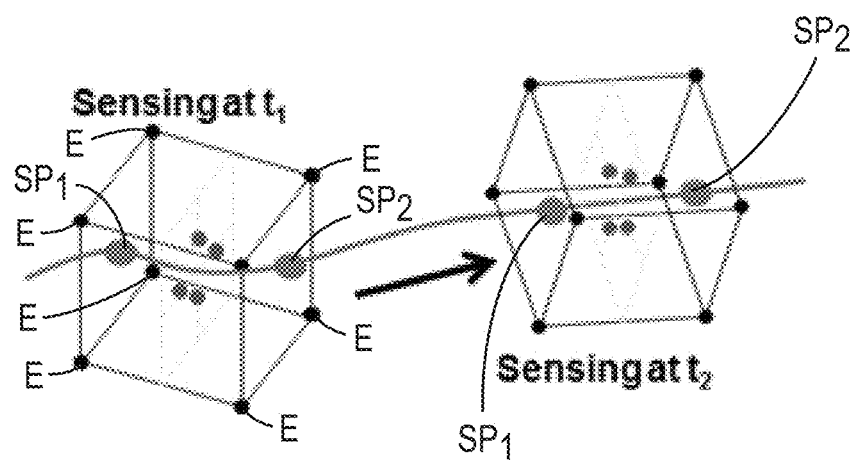
FIG. 15 illustrates filament tracking at a first time, t1, and a second time, t2, in accordance with an example.
Figure 16:
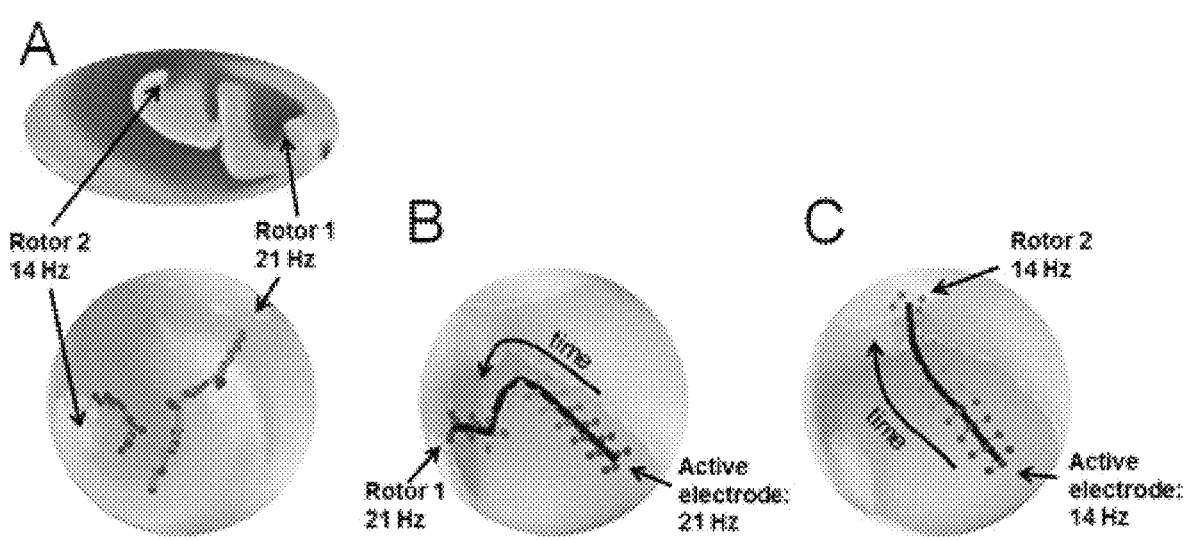
FIG. 16 illustrates another example of filament tracking, in accordance with an example. The cube in this example is guided to be shifted (black arrow designated "time") to the rotor at the highest frequency of 21 Hz.

Next, the processing device may apply a two-prong action. First, a reference fixed potential to one or more of the active electrodes is applied (508). This reference signal is applied to bias the potential distribution within the cavity and determine origin points of activity on the cube faces that would lead to ectopic activity on the heart wall, which in turn could serve as an arrhythmia source. Second, the processing device may also apply harmonic electrical waves to the active electrodes (510), where the phase differences between these harmonic electrical waves generates at least one rotating dipole and singularity point at the highest dominant frequency on the cube faces. To achieve this frequency tuning on the signal may be necessary. The amplitude here may be increased monotonically. The harmonic waves induced at the active electrodes serve to attract an existing filament in the cavity toward the sensing electrodes as illustrated in FIG. 14. Tracing along the filament as shown in FIGS. 15 and 16 would lead toward the area on the wall of a heart that is driving the arrhythmic response. That is, these wall origin points are the initial ectopy or reentry from which waves emanate and propagate to maintain the arrhythmia After the active electrodes have been activated to apply a signal to a target region, the sensed electrical signals are captured by the processing device (512) and the electrodes are turned off (514). A band-pass filtering (from about 3-1 Hz) is then applied to the sensed electrical signals (516). The SVD/R procedure could also be applied in this stage (518). A phase transformation (termed a Hilbert transformation) is subsequently applied (520).

Next, the processing device interpolates phases to create a cubic phase map of the surface joining the sensing electrodes (522). A divergence operator (DO) is applied to the cubic phase map (524). The processing device then examines the cubic phase map to identify longer lasting singularity points (SP, DO is $2\pi$ or approximately $2\pi$) and origin points (OP, DO is 0 or approximately 0) (526).

If origin points are present (528), then the processing device identifies the origin point at the highest dominant frequency (530). If no origin points are identified (532), then the signal amplitude for the reference signal is increased (534) and the process repeats.

If one or more singularity points are present (536), then the processing device determines the singularity point at the highest dominant frequency (538). Otherwise, if no singularity points are present (540), then the signal amplitude is increased for the harmonic electrical waves (542) and the process repeats.

If one or both of an origin point and a singularity point are identified by the processing device, then the processing device may apply a tracking algorithm where the signals applied to the active electrodes are shifted slightly (544), e.g., corresponding to a size smaller than the electrodes, to track the cube origin site or the filament toward the origin point or toward the singularity point at the highest dominant frequency. Then the endocardial wall is reached or when the signal stops progressing in the sample wall (546), the process ends and the identified point sources of arrhythmia are identified.

The catheters described herein may be used has part of an overall endoscopic device for insertion into a subject. For better mechanical control, that endoscopic device (including catheter) may be formed of a posable tubing, for example, endoscopes which may be posable, flexible, steerable, and/or locking ability. That is, locking ability may contribute to better stabilization of the tubing of the apparatus. The endoscope may, for example, be introduced into the left atrium via a minimal incision in the left ventricular free wall. Alternatively, the endoscope may be introduced via a caval route (of, relating to, or characteristic of the vena cava) and transeptal puncture (passing or performed through a septum) to image the left atrium. The presence of a working channel for introduction of recording and ablation catheters (to facilitate the removal of abnormal growths or substances) helped maximize the applicability of the system used.

Combining the catheters herein with optical imaging capability of the endoscope may allow for mapping of at least one anatomical feature and one or more electrical potentials. Specifically, this may include locating anatomical features of the heart including bundles of heart tissue, locating areas of atrial fibrillation, locating veins and arteries, locating weak points of heart tissue, locating valve deficiencies, et cetera. Further, by taking the image or map from inside of the heart, it becomes easier to reconcile cross sectional movement for in vivo analysis (as the heart moves) by lining up the cross section of the anatomical features to understand how the heart tissue displaces during dynamic movement. The anatomical feature map may depict blood vessels, abnormal tissue configuration, tissue bundles, or non-unique homogenous heart tissue.

A map of the electrical potential of a portion of heart tissue will provide a detailed analysis and depiction of the places where a greater electrical potential exists. That is, heart conditions including atrial fibrillation and other arrhythmias may be diagnosed based on abnormal electrical wave propagation through heart tissue.

By having a simultaneous depiction or map of the anatomical features and electrical potential of heart tissue, it is possible to garnish a better understanding of how anatomical features may be indicative of electrical potential differentiations of the heart, or vice versa. Further, the simultaneous map may be in a variety of different orientations with respect to the heart mapping apparatus measurement. That is, the simultaneous map may be a cross sectional view of the anatomical features of the heart and electrical potential of the heart tissue. Or, the simultaneous map may be a surface view of the interior of the heart, penetrating only a few cell layers deep. Or, the simultaneous map may be a three dimensional representation of the subject heart, such that the spatiotemporal and electrical potential are simultaneously depicted by, for example, computer modeling so illustrate how a user's heart functions both physically and electrically when in dynamic motion and operation.

Figure 13:
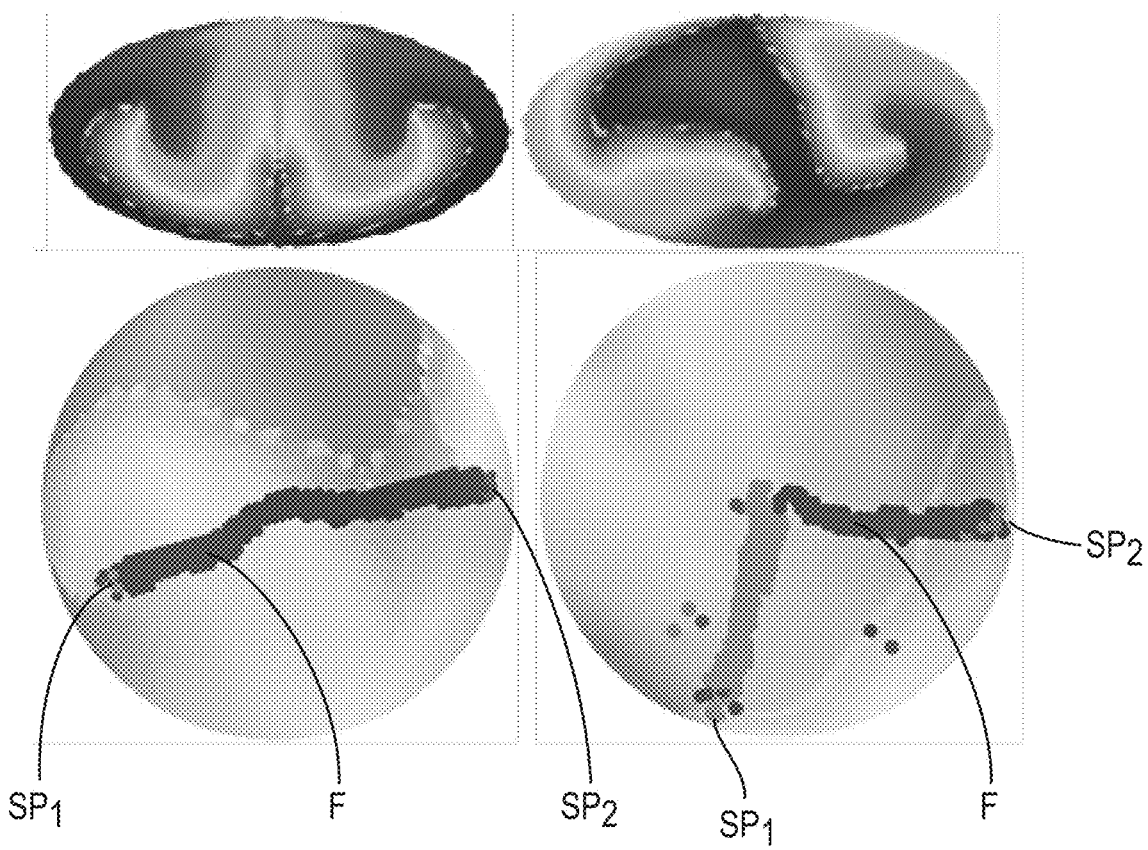
FIG. 13 illustrates filaments formed between phase singularity points for two different rotor examples in the atrial walls of the heart.

FIGS. 13-16 illustrate detection of intracavitary filaments of myocardial rotors using a cubic phase map. FIG. 13 illustrates two test examples used on a spherical shell model of the atria with a passive blood-filled cavity. Filaments (F) are seen stretched between two singularity points (SP1 and SP2) of the rotors on the cardiac wall (the myocardium), in both of the simulations. The singularity points (SP1 and SP) may rotate or change with the rotor in the atrial wall. Therefore, what's depicted is a snapshot of the filaments (F), which were detected by a catheter as shown in FIG. 17, i.e., having 4 active electrodes in a planar square configuration. The first text example, in the left side of FIG. 13, is for a first rotor condition in the atrial walls. The second text example, in the right side of FIG. 13, is for a second rotor condition in the atrial walls.

FIG. 14 illustrates another myocardial rotor filament measuring using a cubic phase map. The left side of FIG. 14 illustrates a filament (F) extending between two singularity points (SP1 and SP2), when no deployable catheter (with electrodes) is present. The filament (F) is almost a linear straight line. On the right side, however, the 4 active electrodes of the catheter of FIG. 17 are present and illustrated by electrode points (E). The presence of these active electrodes produces a rotating dipole that alters the shape of the filament (F). The electrodes may alter the shape of the filament (F) in all three orthogonal planes of the cubic phase map, for example. The filament (F), almost present in the atrial wall, now bends in a central part as affected by the active electrodes of the catheter. The presence of electrodes still leaves the filament (F) substantially in tack at the singularity points (SP1 and SP2), meaning at these outer points the electrodes need not alter the position of the singularity points on the cardiac walls.

In a different embodiment (to the introduction of the HCP in the middle of the 8 electrodes cube) here we introduce 4 active electrodes forming a planner square. Each of the 4 electrodes is generating a harmonic (sine) wave with ¼ sequential phase difference. The result of these 4 waves is a dipole rotating in the plane of the 4 active electrodes. The effect of that rotating dipole on the intracavitary filament produced by the myocardial rotors is simulated and presented in FIG. 14. The figure analyzes the filament stretched between the two similar rotors simulated in a model described in FIG. 14, left panel. On the left side of FIG. 14, no active electrodes are present and the filament is seen to form an almost straight line connecting the two PSs of the rotors on the myocardium. On the right side, 4 active electrodes (black dots) are producing a rotating dipole. That rotating dipole is seen to alter the filament shape that is seen to deviate from the almost straight line in the left panel and is now bent in its central part to pass through the 4 electrodes; at the edges the altered filament is still connected to the PSs of the rotors.

The ability of the active electrodes (e.g., whether 1 active electrode as in FIG. 1 or 4 active electrodes as in FIG. 17) to attract the preexisting filament (F) may depend on the rotating dipole generated by the active electrodes, and more specifically by features of that rotating dipole (controlled by sine-wave signals input to the electrodes), including dipole amplitude and frequency and the chirality of rotation dipole, as well as from the orientation and phase of the dipole relative to the preexisting filament.

FIGS. 15 and 16 illustrate approaches to localizing rotors on the myocardium by tracking intracavitary filaments. In FIG. 15, eight electrodes (E) form an imaginary cube in which sensing of the singularity points (SP1 and SP2) occurs, along with sensing of the filament (F) produced by the combination of myocardial rotors and the rotating dipole generated by the inner active electrodes. Based on the location of the singularity points (SP1 and SP2) on the faces of the sensing cube at time t1, to monitor the shifting of the filament (F), the entire unit cube is shifted to the right along the filament to a new location (see, black arrow) where myocardial rotors and the artificial rotating dipole are sensed again at time t2 to determine the new location of the SP1 and SP2 of the resulted filament.

FIG. 16 demonstrates the performance of an example implementation of the present techniques to localize myocardial rotors from an indiscriminate location inside the heart cavity. Panel A shows a simulation of activity in the spherical atrial model that includes two stable rotors, one rotating at 14 Hz and the other at 21 Hz (modeled by altering the ionic properties in the corresponding hemisphere). The waves emanating from those two rotors collide at the interface between the two hemispheres and generate less stable wavebreaks and phase singularities (SPs). The two rotors also are seen to induce filaments inside the cavity. Panel B and C demonstrate that a sensing-active unit with a rotating dipole at 21 and 14 Hz respectively can be used to track a filament that is the combination of the myocardial and electrode filament toward the location of the corresponding rotor on the myocardial wall.

FIG. 17 is another example catheter device like that of FIG. 1, but having 4 active electrodes (A) and 4 sensing electrodes (S).

Figure 18:
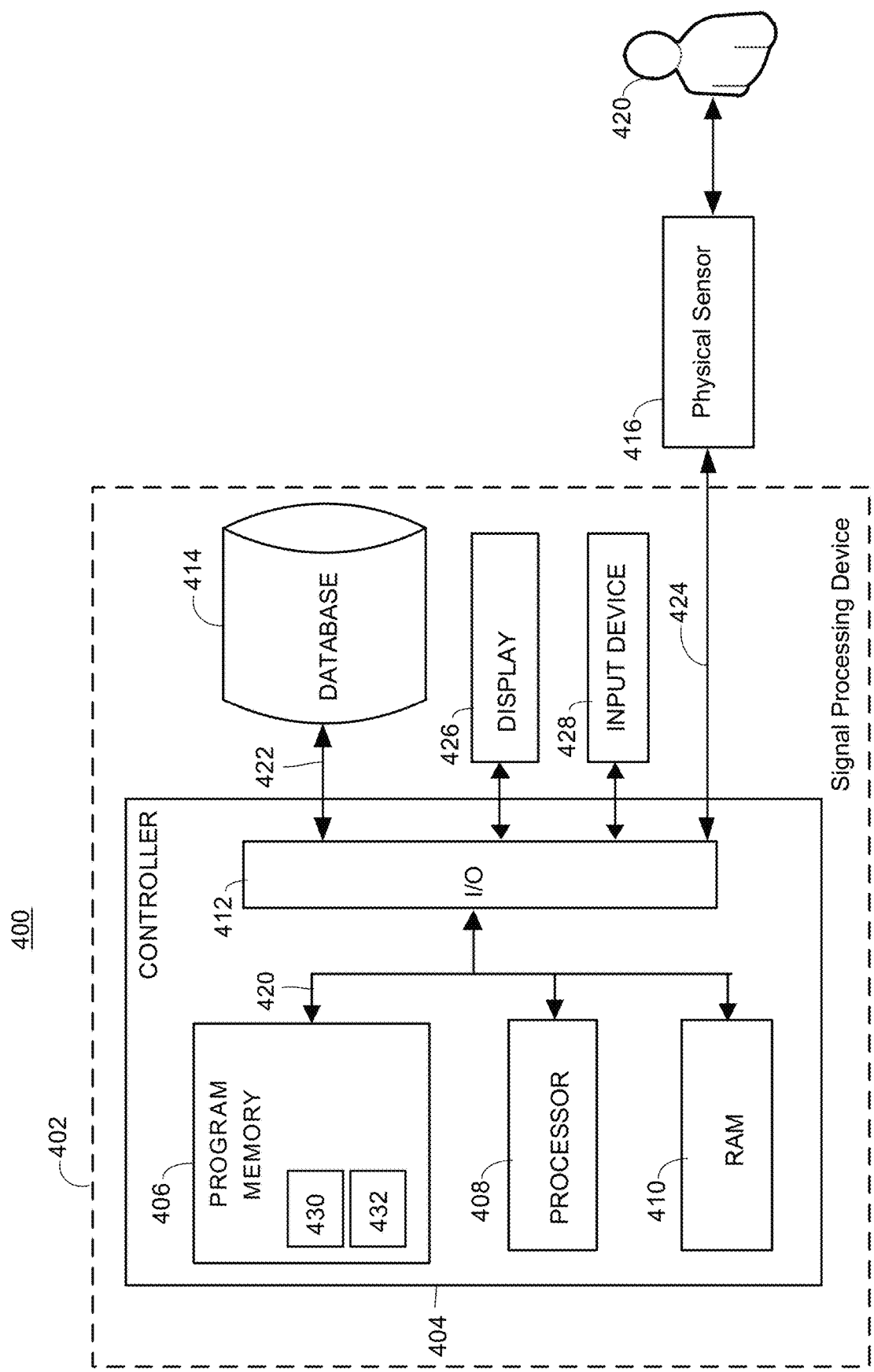
FIG. 18 is a schematic view of an apparatus for mapping electrical cardiac activity and for detecting an ectopy and reentry causing arrhythmia in a heart of a subject.

FIG. 18 is a computer system 400 illustrating the various components used in implementing an example embodiment of the present techniques. By way of example, the system 400 may be implemented in a desktop computer, laptop computer, tablet computer, mobile device smart-phone, network-enabled health monitoring device, cloud based server, an application server, a web server, etc. The computer system 400 may represent a single one of these processing machines or a distributed combination of such processing machines.

A signal processing device 402 (or "signal processor" or "diagnostic device") may be coupled to a patient 420 via one or more geodesic electrode catheter devices in accordance with the teachings herein (e.g., including catheter 102 and 300). The signal processing device 402 may have a controller 404 operatively connected to the database 414 via a link 422 connected to an input/output (I/O) circuit 412. It should be noted that, while not shown, additional databases may be linked to the controller 404 in a known manner. The controller 404 includes a program memory 406, one or more processors 408 (may be called microcontrollers or a microprocessors), a random-access memory (RAM) 410, and the input/output (I/O) circuit 412, all of which are interconnected via an address/data bus 420. It should be appreciated that although only one processor 408 is shown, the controller 404 may include multiple microprocessors 408. Similarly, the memory of the controller 404 may include multiple RAMs 410 and multiple program memories 406. Although the I/O circuit 412 is shown as a single block, it should be appreciated that the I/O circuit 412 may include a number of different types of I/O circuits. The RAM(s) 410 and the program memories 406 may be implemented as semiconductor memories, magnetically readable memories, and/or optically readable memories, for example. A link 424, which may include one or more wired and/or wireless (Bluetooth, WLAN, etc.) connections, may operatively connect the controller 404 to a physical sensor assembly 416 through the I/O circuit 412. The sensor assembly 416 may include a catheter as described herein and that is inserted into the patient 420, as well as a sensor controller that activates and controls that catheter. Reference number 416, therefore, may be used in reference to any number of these elements of the sensor assembly.

The program memory 406 and/or the RAM 410 may store various applications (i.e., machine readable instructions) for execution by the processor 408. For example, an operating system 430 may generally control the operation of the signal processing device 402 and provide a user interface to the signal processing device 402 to implement the stages of the configurations 100 and 100' described herein. The program memory 406 and/or the RAM 410 may also store a variety of subroutines 432 for accessing specific functions of the signal processing device 402. By way of example, and without limitation, the subroutines 432 may include, among other things: a subroutine for collecting electrical signal data from electrodes in the catheter 416, a subroutine for filtering the electrical signal data from the electrodes in the catheter 416, a subroutine performing singularity value decomposition and reconstruction filtering on the electrical signal data, subroutine for linearly interpolating the electrical signal data, subroutine for applying phase transformation to electrical signal data and developing a cubic phase map of the transformed electrical signal data, and subroutine for identifying within the cubic phase map singularity points indicating a filament of electrical activity a region of interest (such as the heart, atriums and/or ventricles). The subroutines 432 may include a subroutine to generate a health report and/or alarm condition, for example, using the display 426. That health report and/or alarm condition may be displayed as a web page, mobile device alert, tactile alert or alarm (e.g., via a vibrating function of a smartwatch or smartphone), or any other suitable visual and/or tactile display. The subroutines 432 may communicate this health report and/or alarm condition to a separate computing device connected to the system 100 through a network connection. Such separate computing devices may include a server, laptop computer, handheld computer, health monitor, mobile device such as a cellular phone or Wi-Fi-enabled tablet, or other device. The subroutines 432 may include a subroutine to communicate the mapped electrical activity data or a health report, alarm condition, or other analysis thereof to a treatment system, such as therapeutic delivery system for administering a therapeutic treatment to a subject. The subroutines 432 may also include other subroutines, for example, implementing software keyboard functionality, interfacing with other hardware in the signal processing device 402, etc. The program memory 406 and/or the RAM 410 may further store data related to the configuration and/or operation of the signal processing device 402, and/or related to the operation of the one or more subroutines 432. For example, the data may be data gathered by the catheter 416, data determined and/or calculated by the processor 408, etc. In addition to the controller 404, the signal processing device 402 may include other hardware resources. The signal processing device 402 may also include various types of input/output hardware such as a visual display 426 and input device(s) 428 (e.g., keypad, keyboard, etc.). In an embodiment, the display 426 is touch-sensitive, and may cooperate with a software keyboard routine as one of the software routines 432 to accept user input.

It may be advantageous for the signal processing device 402 to communicate with a broader medical treatment network (not shown) through any of a number of known networking devices and techniques (e.g., through a computer network such as a hospital or clinic intranet, the Internet, etc.). For example, the apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Although depicted as separate entities or components in FIG. 18, it is understood that any or all of the signal processing functionality and/or components of the signal processing device 402 may be combined with an electrical activity monitoring device, such as within an ECG monitoring machine. In this manner, the system 400 may both gather data about the patient 420 and process the gathered data to extract one or more features. Also, although depicted as a single component in FIG. 1, the catheter 416 may include multiple of the same type or different types of catheters and the catheter 416 may represent an endoscopic device including imagining functionality, ablation functionality, etc. and combinations thereof.

Figure 19:
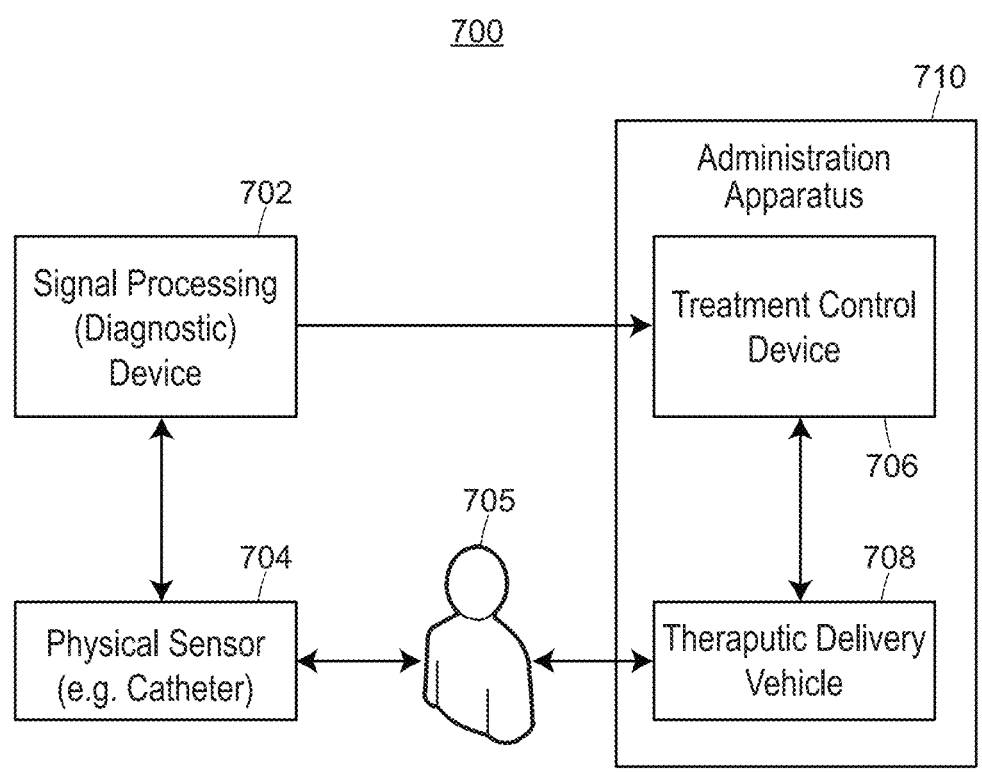
FIG. 19 is a schematic of a therapeutic delivery system for administering a therapeutic treatment to a subject using the apparatus of FIG. 18, in a closed loop manner.

FIG. 19 illustrates an example closed loop system 700 in which a therapeutic treatment may be administered in response to a stored one or more extracted features. A signal processing (diagnostic) device 702 (e.g., device 402) is coupled to a catheter 704 (e.g., 416) to monitor a subject 705 and to determine a filament causing arrhythmia in a heart of a subject, e.g., determining where the filament is for ablation treatment. A treatment control device 706 (such as an ablation device or a drug administration device) is coupled to therapeutic delivery vehicle 708, both of which are part of an administration apparatus 710. The components are coupled in a closed loop manner, such that the catheter 704 probes the subject 705 and communicates with the signal processing device 702 (part of a diagnostic apparatus) that assesses an arrhythmia or other condition in a target region. That identification may be provided to the treatment administration apparatus 710 that includes the treatment control device 706, which upon receiving data indicating a sufficient condition for the subject, instructs the therapeutic delivery vehicle 708 to administer a therapeutic treatment to the subject 705, to address the subject's condition.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A catheter comprising: a housing extending from a proximal end to a distal end configured for insertion into a target region of a subject, the housing having an inner wall, wherein the housing is hollow and open at the distal end; and a plurality of electrodes positioned within the housing and spaced apart from one another, the plurality of electrodes extending from the proximal end to the distal end, each electrode of the plurality of electrodes providing an electrical conduction path between the distal end and the proximal end, and wherein the plurality of electrodes are positioned such that collectively the plurality of electrodes provide electrical conduction paths over a portion of the target region, and wherein the catheter is configured to maintain a geometric configuration between the plurality of electrodes when the distal end of the catheter is deployed within the subject, wherein the plurality of electrodes comprises, an active electrode structure, containing at least one active electrode, configured to provide an activation signal to the portion of the target region, and a sensing electrode structure, containing a plurality of sensing electrodes, configured to sense a resulting signal propagating in the target region, the plurality of sensing electrodes having respective end points which are axially spaced apart that correspond to vertices defining a 3-dimensional volumetric space, wherein the active electrode structure is positioned inside the sensing electrode structure and a central axis of the active electrode structure defines a central axis of the catheter, wherein, at the distal end, each of the plurality of sensing electrodes of the sensing electrode structure is equidistant from the central axis of the catheter, and wherein the at least one active electrode of the active electrode structure is closer to the central axis than the plurality of sensing electrodes, and wherein, at the distal end, the at least one active electrode is suspended in free space independent of the housing and maintained free from contact with the target region.

2. The catheter of claim 1, wherein the plurality of sensing electrodes are evenly spaced within the housing and terminate, at the distal end, by extending into respective receptacles around a wall of the housing or by extending adjacent to the wall of the housing.

3. The catheter of claim 1, wherein the number of the plurality of electrodes and the position of the plurality of electrodes are such that the catheter provides conduction paths over a full circumferential area within the target region of the subject.

4. The catheter of claim 3, wherein the plurality of electrodes are positioned such that the catheter provides conduction paths over a circumferential volume within the target region of the subject.

5. The catheter of claim 1, wherein the subject is the heart and the target region is the atrium or ventricle of the heart.

6. The catheter of claim 1, wherein the sensing electrode structure comprises eight electrodes.

7. The catheter of claim 1, wherein the plurality of sensing electrodes share a common electrical ground.

8. The catheter of claim 7, wherein the at least one active electrode is a high conductance pole electrode.

9. The catheter of claim 8, wherein the high conductance pole electrode is connected to a power supply that generates a coordinated time fixed or time varying potential to create a mono-polar or multi-polar source configuration inside a cavity.

10. The catheter of claim 1, wherein the at least one active electrode has an electrical ground isolated from the plurality of sensing electrodes.

11. The catheter of claim 1, wherein the plurality of sensing electrodes are grounded to the housing and wherein the at least one active electrode is free for grounding to an external ground.

12. The catheter of claim 1, wherein a space between the plurality of electrodes is free for receiving fluid.

13. The catheter of claim 1, further comprising a plurality of fluid inlet/outlet openings to allow for fluid flow through the catheter.

14. The catheter of claim 13, wherein at least one of the plurality of fluid inlet/outlet openings extends through an outer side wall of the housing.

15. The catheter of claim 13, wherein at least one of the plurality of fluid inlet/outlet openings extends through the distal end of the housing.

16. The catheter of claim 1, wherein the active electrode structure comprises the at least one active electrode positioned on the central axis of the catheter and equidistant from the plurality of sensing electrodes.

17. The catheter of claim 1, wherein the active electrode structure comprises four active electrodes positioned equidistantly from the central axis of the catheter and centrally within the sensing electrode structure.

18. The catheter of claim 1, wherein the respective end points of the plurality of sensing electrodes correspond to vertices of a cubic space.

19. The catheter of claim 1, wherein there are four (4) or eight (8) sensing electrodes, the respective end points of the 4 or 8 sensing electrodes corresponding to the vertices defining the 3-dimensional volumetric space.

20. A system for mapping electrical cardiac activity, the system comprising: a catheter comprising, a housing extending from a proximal end to a distal end configured for insertion into a target region of a subject, the housing having an inner wall, wherein the housing is hollow and open at the distal end; a plurality of electrodes positioned within the housing and spaced apart from one another, the plurality of electrodes extending from the proximal end to the distal end, each electrode of the plurality of electrodes providing an electrical conduction path between the distal end and the proximal end, and wherein the plurality of electrodes are positioned such that collectively the plurality of electrodes provide electrical conduction paths over a portion of the target region, wherein the catheter is configured to maintain a geometric configuration between the plurality of electrodes when the distal end of the catheter is deployed within the subject, wherein the plurality of electrodes comprises, an active electrode structure, containing at least one active electrode, configured to provide an activation signal to the portion of the target region, and a sensing electrode structure, containing a plurality of sensing electrodes, configured to sense a resulting signal propagating in the target region, the plurality of sensing electrodes having respective end points which are axially spaced apart that correspond to vertices defining a 3-dimensional volumetric space, wherein the active electrode structure is positioned inside the sensing electrode structure and a central axis of the active electrode structure defines a central axis of the catheter, wherein, at the distal end, each of the plurality of sensing electrodes of the sensing electrode structure is equidistant from the central axis of the catheter, and wherein the at least one active electrode of the active electrode structure is closer to the central axis than the plurality of sensing electrodes, and wherein, at the distal end, the at least one active electrode is suspended in free space independent of the housing and maintained free from contact with the target region; one or more processors coupled to the plurality of electrodes of the catheter; and one or more non-transitory computer readable memories coupled to the one or more processors, wherein the one or more memories include computer-executable instructions stored therein that, when executed by the one or more processors, cause the one or more processors to, provide an activation signal to the at least one active electrode to supply conduction input to the portion of the target region, receive electrical signal data from at least some of the plurality of sensing electrodes, identify electrical signal nodes in the received electrical signal data, develop a 3-dimensional cubic phase map from the electrical signal data, wherein the 3-dimensional cubic phase map includes an indication of the identified electrical signal nodes, and display the 3-dimensional cubic phase map.

21. The system of claim 20, wherein the subject is the heart and the target region in an atrium or ventricle, wherein the one or more memories include computer-executable instructions stored therein that, when executed by the one or more processors, cause the one or more processors to:

identify a location of one or more rotors of electrical activity in the target region, the rotors indicating a source of arrhythmia in the target region; or identify a location of one or more ectopies of electrical activity in the target region, the ectopies indicating a source of arrhythmia in the target region.

22. The system of claim 20, wherein the one or more memories include computer-executable instructions stored therein that, when executed by the one or more processors, cause the one or more processors to:

track changes in one or more filaments, by (i) receiving electrical signal data from the plurality of sensing electrodes of the catheter over a sampling window of time, (ii) identifying electrical signal nodes in the received electrical signal data over the sampling window of time, and (iii) tracking the electrical signal nodes over the cubic phase map over the sampling window of time.

23. The system of claim 20, wherein the one or more memories include computer-executable instructions stored therein that, when executed by the one or more processors, cause the one or more processors to:

stabilize the electrical signal data from the plurality of sensing electrodes, using the activation signal provided to the at least one active electrode.

* * * * *